(12) United States Patent
Joseph

(10) Patent No.: US 8,951,217 B2
(45) Date of Patent: Feb. 10, 2015

(54) COMPOSITE MATERIAL FOR CUSTOM FITTED PRODUCTS

(75) Inventor: Mark Joseph, Aspen, CO (US)

(73) Assignee: EXOS LLC, Vista, CA (US)

( * ) Notice: Subject to any disclaimer, the term of this patent is extended or adjusted under 35 U.S.C. 154(b) by 3 days.

(21) Appl. No.: 13/217,083

(22) Filed: Aug. 24, 2011

(65) Prior Publication Data

US 2012/0101417 A1 Apr. 26, 2012

Related U.S. Application Data

(63) Continuation of application No. PCT/US2010/025119, filed on Feb. 23, 2010, which is a continuation-in-part of application No. 12/710,252, filed on Feb. 22, 2010, now abandoned, and a continuation of application No. 12/711,188, filed on Feb. 23, 2010, now abandoned, which is a continuation-in-part of application No. 12/710,252, filed on Feb. 22, 2010, now abandoned.

(60) Provisional application No. 61/155,138, filed on Feb. 24, 2009.

(51) Int. Cl.
| A61F 5/00 | (2006.01) |
| A61F 5/01 | (2006.01) |
| A61F 5/055 | (2006.01) |
| A61F 5/058 | (2006.01) |
| B29C 51/00 | (2006.01) |
| B29C 51/42 | (2006.01) |
| B29L 31/00 | (2006.01) |

(52) U.S. Cl.
CPC .................. *A61F 5/01* (2013.01); *A61F 5/0104* (2013.01); *A61F 5/0118* (2013.01); *A61F 5/055* (2013.01); *A61F 5/058* (2013.01); *B29C 51/00* (2013.01); *B29C 51/008* (2013.01); *B29C 51/421* (2013.01); *B29L 2031/753* (2013.01)
USPC ............. 602/7; 602/5; 602/6; 602/20; 602/21

(58) Field of Classification Search
USPC ................................................... 602/5–10, 21
See application file for complete search history.

(56) References Cited

U.S. PATENT DOCUMENTS

| 57,283 A | 8/1866 | Brown |
| D19,360 S | 10/1889 | Sanders |

(Continued)

FOREIGN PATENT DOCUMENTS

| CN | 2902232 | 5/2007 |
| CN | 101279110 | 10/2008 |

(Continued)

OTHER PUBLICATIONS

PCT Patent Application No. PCT/US2010/25119; filed Feb. 23, 2010; Applicant Exos Corporation; International Search Report dated Jul. 26, 2010.

(Continued)

*Primary Examiner* — Kim M Lewis
(74) *Attorney, Agent, or Firm* — Knobbe, Martens, Olson & Bear LLP

(57) ABSTRACT

A composite material for forming custom fitted orthopedic and other products. The composite material is easily formable when heated to temperatures of about two hundred degrees Fahrenheit for a time of at least six to eight minutes and then is rigid at temperatures of about one hundred thirty degrees. The composite material can be sewn and formed in complex shapes when initially heated to about two hundred degrees. Closure attachments can be secured to the composite material as needed on site rather than at the manufacturing facility. The composite material can be custom fitted to a patient in situ.

24 Claims, 28 Drawing Sheets

(56) References Cited

U.S. PATENT DOCUMENTS

| | | | |
|---|---|---|---|
| 482,647 A | 9/1892 | Obear | |
| D35,545 S | 12/1901 | Schaefer | |
| 975,734 A | 11/1910 | Tebeau | |
| 1,082,542 A | 12/1913 | Manson | |
| 1,360,840 A | 11/1920 | White | |
| 1,471,948 A | 10/1923 | Cox et al. | |
| 1,583,606 A | 5/1926 | Roussel | |
| 2,070,810 A | 2/1937 | Saling | |
| 2,181,689 A | 11/1939 | Bell | |
| 2,206,404 A | 7/1940 | Jones | |
| 2,477,040 A | 3/1945 | Brown et al. | |
| 2,554,337 A | 5/1951 | Lampert | |
| 2,736,314 A | 2/1956 | Hale | |
| 2,759,475 A | 8/1956 | Swaay | |
| 2,818,063 A | 12/1957 | Smith et al. | |
| 2,904,040 A | 9/1959 | Hale | |
| D198,069 S | 4/1964 | Connelly | |
| D203,018 S | 11/1965 | Helferich | |
| 3,302,642 A | 2/1967 | Allen | |
| 3,306,284 A | 2/1967 | McKinley | |
| 3,313,297 A | 4/1967 | Applegate et al. | |
| 3,320,950 A | 5/1967 | McElvenny | |
| 3,420,231 A | 1/1969 | Edenbaum | |
| 3,490,444 A | 1/1970 | Larson | |
| 3,512,523 A | 5/1970 | Barnett | |
| 3,692,023 A | 9/1972 | Phillips et al. | |
| 3,788,307 A | 1/1974 | Kistner | |
| 3,896,843 A | 7/1975 | Millar et al. | |
| 3,906,943 A | 9/1975 | Arluck | |
| 3,916,885 A | 11/1975 | Gaylord, Jr. | |
| 3,924,272 A | 12/1975 | Allen et al. | |
| 4,006,741 A | 2/1977 | Arluck | |
| 4,019,505 A | 4/1977 | Wartman | |
| 4,136,686 A | 1/1979 | Arluck | |
| 4,169,469 A | 10/1979 | Arluck | |
| 4,193,395 A | 3/1980 | Gruber | |
| D256,055 S | 7/1980 | Finnieston | |
| 4,235,228 A | 11/1980 | Gaylord | |
| 4,240,415 A | 12/1980 | Wartman | |
| D259,955 S | 7/1981 | Helferich | |
| 4,286,586 A | 9/1981 | Potts | |
| 4,316,457 A | 2/1982 | Liegeois | |
| D266,288 S | 9/1982 | Coon | |
| D270,284 S | 8/1983 | Lindh et al. | |
| 4,427,002 A | 1/1984 | Baron et al. | |
| 4,441,711 A | 4/1984 | Dubar et al. | |
| 4,442,834 A | 4/1984 | Tucker et al. | |
| 4,454,873 A | 6/1984 | Laufenberg et al. | |
| 4,471,993 A | 9/1984 | Watson | |
| 4,473,671 A | 9/1984 | Green | |
| 4,483,333 A | 11/1984 | Wartman | |
| 4,510,927 A | 4/1985 | Peters | |
| 4,531,241 A | 7/1985 | Berger | |
| 4,572,167 A | 2/1986 | Brunswick | |
| 4,584,993 A | 4/1986 | Nelson | |
| 4,600,618 A | 7/1986 | Raychok, Jr. et al. | |
| D287,640 S | 1/1987 | Primiano | |
| 4,661,535 A | 4/1987 | Borroff | |
| 4,765,319 A | 8/1988 | Finnieston et al. | |
| 4,770,299 A | 9/1988 | Parker | |
| 4,784,123 A | 11/1988 | Robeson | |
| 4,827,915 A | 5/1989 | Gorsen | |
| 4,888,225 A | 12/1989 | Sandvig et al. | |
| 4,912,174 A | 3/1990 | Grouiller | |
| 4,946,726 A | 8/1990 | Sandvig et al. | |
| 4,955,368 A | 9/1990 | Heimann | |
| 5,031,607 A | 7/1991 | Peters | |
| 5,038,759 A | 8/1991 | Morgenstern | |
| 5,058,576 A | 10/1991 | Grim et al. | |
| D326,719 S | 6/1992 | Eghamn | |
| 5,158,098 A | 10/1992 | Jalalian | |
| 5,180,361 A | 1/1993 | Moore et al. | |
| 5,230,698 A | 7/1993 | Garth | |
| 5,316,604 A | 5/1994 | Fell | |
| RE34,714 E | 8/1994 | Burns et al. | |
| 5,364,693 A | 11/1994 | Moren et al. | |
| 5,366,439 A | 11/1994 | Peters | |
| D357,745 S | 4/1995 | Radwell | |
| 5,415,622 A | 5/1995 | Kelley | |
| D363,780 S | 10/1995 | Darby et al. | |
| 5,454,780 A | 10/1995 | Duback et al. | |
| 5,520,529 A | 5/1996 | Heckel | |
| D373,639 S | 9/1996 | McKie | |
| 5,554,104 A | 9/1996 | Grim | |
| 5,599,288 A | 2/1997 | Shirley et al. | |
| 5,624,386 A | 4/1997 | Tailor et al. | |
| 5,632,722 A | 5/1997 | Tweardy et al. | |
| 5,688,229 A | 11/1997 | Bauer | |
| 5,737,774 A | 4/1998 | Petty-Saphon et al. | |
| 5,752,873 A | 5/1998 | Morris | |
| 5,752,926 A | 5/1998 | Larson et al. | |
| D395,514 S | 6/1998 | Stano | |
| 5,769,804 A | 6/1998 | Harris et al. | |
| 5,807,291 A | 9/1998 | Larson et al. | |
| 5,826,304 A | 10/1998 | Carlson | |
| 5,830,167 A | 11/1998 | Jung | |
| D405,180 S | 2/1999 | Reina | |
| 5,865,778 A | 2/1999 | Johnson | |
| 5,882,322 A | 3/1999 | Kim et al. | |
| 5,902,259 A | 5/1999 | Wilkerson | |
| 5,934,599 A | 8/1999 | Hammerslag | |
| 5,951,504 A | 9/1999 | Iglesias et al. | |
| 5,971,946 A | 10/1999 | Quinn et al. | |
| 5,982,285 A | 11/1999 | Bueche et al. | |
| 6,042,557 A | 3/2000 | Ferguson et al. | |
| 6,053,884 A | 4/2000 | Peters | |
| 6,056,671 A | 5/2000 | Marmer | |
| 6,056,713 A | 5/2000 | Hayashi | |
| RE36,745 E | 6/2000 | Rudy, Jr. et al. | |
| 6,093,161 A | 7/2000 | Vlaeyen et al. | |
| 6,110,134 A | 8/2000 | Clark, Jr. et al. | |
| 6,146,240 A | 11/2000 | Morris | |
| D436,177 S | 1/2001 | Miller | |
| D437,416 S | 2/2001 | Slautterback | |
| 6,186,966 B1 | 2/2001 | Grim et al. | |
| 6,202,953 B1 | 3/2001 | Hammerslag | |
| 6,254,560 B1 | 7/2001 | Tweardy et al. | |
| 6,289,558 B1 | 9/2001 | Hammerslag | |
| 6,322,529 B1 | 11/2001 | Chung | |
| 6,325,772 B1 | 12/2001 | Scheuermann et al. | |
| 6,358,220 B1 | 3/2002 | Langen et al. | |
| 6,416,074 B1 | 7/2002 | Maravetz et al. | |
| 6,423,020 B1 | 7/2002 | Koledin | |
| D463,565 S | 9/2002 | Slautterback | |
| 6,520,925 B1 | 2/2003 | Thibodo, Jr. | |
| D473,653 S | 4/2003 | Weaver, II et al. | |
| D477,088 S | 7/2003 | Brown et al. | |
| D477,409 S | 7/2003 | Mills et al. | |
| D477,410 S | 7/2003 | Wiggins et al. | |
| 6,602,215 B1 | 8/2003 | Richie, Jr. | |
| 6,663,581 B1 | 12/2003 | Calabrese | |
| D492,787 S | 7/2004 | Weaver, II et al. | |
| 6,779,282 B2 | 8/2004 | Grohninger | |
| D496,465 S | 9/2004 | Weaver, II | |
| D500,855 S | 1/2005 | Pick et al. | |
| 6,843,190 B1 | 1/2005 | LaPierre-McAfee | |
| 6,872,188 B2 | 3/2005 | Caille et al. | |
| D505,727 S | 5/2005 | Krahner et al. | |
| 6,893,410 B1 | 5/2005 | Hely | |
| 6,922,917 B2 | 8/2005 | Kerns et al. | |
| 6,960,176 B1 | 11/2005 | Hely et al. | |
| 7,001,348 B2 | 2/2006 | Garth et al. | |
| D518,895 S | 4/2006 | Weaver, II et al. | |
| D519,211 S | 4/2006 | Doty et al. | |
| 7,025,737 B2 | 4/2006 | Modglin | |
| 7,041,073 B1 | 5/2006 | Patron | |
| 7,056,298 B1 | 6/2006 | Weber | |
| 7,082,701 B2 | 8/2006 | Dalgaard et al. | |
| 7,083,585 B2 | 8/2006 | Latham | |
| 7,090,653 B2 | 8/2006 | Moeller | |
| D530,016 S | 10/2006 | Sroufe et al. | |
| 7,141,031 B2 | 11/2006 | Garth et al. | |
| 7,182,741 B2 | 2/2007 | Porrata et al. | |
| 7,204,817 B1 | 4/2007 | Toronto et al. | |

(56) References Cited

U.S. PATENT DOCUMENTS

| | | |
|---|---|---|
| D542,919 S | 5/2007 | Leatt |
| 7,217,060 B2 | 5/2007 | Ingimarsson |
| D550,370 S | 9/2007 | Peters et al. |
| D552,743 S | 10/2007 | Verkade et al. |
| D552,744 S | 10/2007 | Verkade et al. |
| D558,883 S | 1/2008 | Ortiz et al. |
| 7,316,660 B1 | 1/2008 | Modglin |
| 7,329,229 B2 | 2/2008 | Scheinberg et al. |
| D565,189 S | 3/2008 | Gramza et al. |
| 7,392,602 B2 | 7/2008 | Reagan et al. |
| 7,399,288 B2 | 7/2008 | Chao |
| D580,064 S | 11/2008 | Lin et al. |
| D580,555 S | 11/2008 | Lin et al. |
| 7,449,006 B2 | 11/2008 | Wolanske |
| 7,470,243 B2 | 12/2008 | Garth |
| D584,822 S | 1/2009 | Weber |
| 7,507,215 B2 | 3/2009 | Ryan |
| 7,591,050 B2 | 9/2009 | Hammerslag |
| 7,597,671 B2 | 10/2009 | Baumgartner et al. |
| 7,608,052 B1 | 10/2009 | Baker |
| 7,645,250 B2 | 1/2010 | Koby et al. |
| 7,674,234 B2 | 3/2010 | Calco et al. |
| D616,556 S | 5/2010 | Hu |
| D617,464 S | 6/2010 | Weaver, II et al. |
| 7,727,172 B2 | 6/2010 | Wang |
| D626,242 S | 10/2010 | Sagnip et al. |
| D626,244 S | 10/2010 | Sagnip et al. |
| D628,300 S | 11/2010 | Caden |
| D628,696 S | 12/2010 | Robertson |
| D629,115 S | 12/2010 | Robertson |
| 7,846,118 B2 | 12/2010 | Sandhu |
| 7,854,714 B1 | 12/2010 | Weber et al. |
| 7,874,997 B2 | 1/2011 | Jaccard |
| D632,401 S | 2/2011 | Stevens |
| 7,883,485 B2 | 2/2011 | Moenning et al. |
| D633,622 S | 3/2011 | Chiang |
| D633,623 S | 3/2011 | Leatt et al. |
| D635,269 S | 3/2011 | Franke et al. |
| D635,270 S | 3/2011 | Chiang |
| D635,682 S | 4/2011 | Chiang |
| D636,494 S | 4/2011 | Garth et al. |
| D638,948 S | 5/2011 | Janzon |
| 7,942,837 B2 | 5/2011 | Clark et al. |
| 7,950,112 B2 | 5/2011 | Hammerslag et al. |
| D639,965 S | 6/2011 | Wehsely-Swiczinsky |
| 7,954,204 B2 | 6/2011 | Hammerslag et al. |
| 7,955,287 B2 | 6/2011 | Frangi |
| D641,482 S | 7/2011 | Robertson et al. |
| D641,483 S | 7/2011 | Robertson et al. |
| D643,978 S | 8/2011 | Alonso et al. |
| 7,992,261 B2 | 8/2011 | Hammerslag et al. |
| D647,623 S | 10/2011 | Thorgilsdottir et al. |
| D647,624 S | 10/2011 | Thorgilsdottir et al. |
| D649,648 S | 11/2011 | Cavalieri et al. |
| D649,649 S | 11/2011 | Leatt et al. |
| D649,650 S | 11/2011 | Wehsely-Swiczinsky |
| 8,057,417 B2 | 11/2011 | Imai |
| D650,485 S | 12/2011 | Jaccard |
| D652,937 S | 1/2012 | Robertson et al. |
| 8,091,182 B2 | 1/2012 | Hammerslag et al. |
| D654,180 S | 2/2012 | Weaver, Ii |
| D657,062 S | 4/2012 | Chiang |
| D657,063 S | 4/2012 | Chiang |
| D663,850 S | 7/2012 | Joseph |
| D663,851 S | 7/2012 | Joseph |
| D663,852 S | 7/2012 | Joseph |
| D664,259 S | 7/2012 | Joseph |
| D665,088 S | 8/2012 | Joseph |
| D666,301 S | 8/2012 | Joseph |
| D666,302 S | 8/2012 | Joseph |
| 8,246,560 B2 | 8/2012 | Gaylord et al. |
| 8,277,401 B2 | 10/2012 | Hammerslag et al. |
| 8,303,527 B2 | 11/2012 | Joseph |
| D687,556 S | 8/2013 | Joseph |
| 2002/0068890 A1 | 6/2002 | Schwenn et al. |
| 2002/0095750 A1 | 7/2002 | Hammerslag |
| 2002/0148461 A1 | 10/2002 | Heinz et al. |
| 2002/0161114 A1 | 10/2002 | Gunatillake et al. |
| 2003/0178404 A1 | 9/2003 | Dimartino et al. |
| 2003/0204938 A1 | 11/2003 | Hammerslag |
| 2004/0024337 A1 | 2/2004 | Tseng et al. |
| 2005/0034686 A1 | 2/2005 | Spatt |
| 2005/0043664 A1 | 2/2005 | Reaux |
| 2005/0101898 A1 | 5/2005 | Cohen |
| 2005/0197606 A1 | 9/2005 | Preire |
| 2005/0273030 A1 | 12/2005 | Koby et al. |
| 2005/0281999 A1 | 12/2005 | Hofmann et al. |
| 2006/0051402 A1 | 3/2006 | Bogardus et al. |
| 2006/0052730 A1 | 3/2006 | Hargrave et al. |
| 2006/0062991 A1 | 3/2006 | Sendijarevic et al. |
| 2006/0129075 A1 | 6/2006 | Scheinberg et al. |
| 2006/0155226 A1 | 7/2006 | Grim et al. |
| 2006/0156517 A1 | 7/2006 | Hammerslag et al. |
| 2007/0004993 A1 | 1/2007 | Coppens et al. |
| 2007/0077393 A1 | 4/2007 | Chiang et al. |
| 2007/0179417 A1 | 8/2007 | Schwenn et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0082033 A1 | 4/2008 | Ortiz |
| 2008/0083135 A1 | 4/2008 | Hammerslag et al. |
| 2008/0177210 A1 | 7/2008 | McDevitt Larson |
| 2008/0262400 A1* | 10/2008 | Clark et al. ............... 602/7 |
| 2008/0319362 A1 | 12/2008 | Joseph |
| 2009/0082707 A1 | 3/2009 | Rumsey |
| 2009/0192425 A1 | 7/2009 | Garth et al. |
| 2009/0192427 A1 | 7/2009 | Brown et al. |
| 2009/0204047 A1 | 8/2009 | MacArthur |
| 2009/0264802 A1 | 10/2009 | Chen |
| 2010/0168630 A1 | 7/2010 | Cropper et al. |
| 2010/0185130 A1 | 7/2010 | Rizo Patron |
| 2010/0262054 A1 | 10/2010 | Summit et al. |
| 2010/0268139 A1 | 10/2010 | Garth |
| 2010/0268140 A1 | 10/2010 | Berlese |
| 2010/0268141 A1 | 10/2010 | Bannister |
| 2010/0299959 A1 | 12/2010 | Hammerslag et al. |
| 2010/0318010 A1 | 12/2010 | Sandifer et al. |
| 2011/0034844 A1 | 2/2011 | Thorgilsdottir et al. |
| 2011/0082402 A1 | 4/2011 | Oddou et al. |
| 2011/0130694 A1 | 6/2011 | Livolsi et al. |
| 2011/0213284 A1 | 9/2011 | Garth et al. |
| 2012/0065562 A1 | 3/2012 | Kaphingst |
| 2013/0102940 A1 | 4/2013 | Joseph |

FOREIGN PATENT DOCUMENTS

| | | |
|---|---|---|
| EP | 0 393 003 A1 | 10/1990 |
| EP | 0401883 A1 | 12/1990 |
| EP | 0625342 A1 | 11/1994 |
| EP | 0 795 307 | 4/2004 |
| JP | 09-234241 | 9/1997 |
| JP | 2004-065912 | 3/2004 |
| WO | WO 93/21967 | 11/1993 |
| WO | WO 2007/035875 | 3/2007 |
| WO | WO 2007035875 A1 | 3/2007 |
| WO | WO 2010/099130 | 9/2010 |
| WO | WO 2011/071264 | 6/2011 |
| WO | WO 2012/138523 | 10/2012 |

OTHER PUBLICATIONS

PCT Patent Application No. PCT/US2010/25119; filed Feb. 23, 2010; Applicant Exos Corporation; Written Opinion dated Jul. 26, 2010.

PCT Patent Application No. PCT/US2008/067570; filed Jun. 19, 2008; Applicant Product Innovations, Inc.; International Search Report dated Oct. 10, 2008.

PCT Patent Application No. PCT/US2008/067570; filed Jun. 19, 2008; Applicant Product Innovations, Inc.; Written Opinion dated Oct. 10, 2008.

(56) References Cited

OTHER PUBLICATIONS

Application and File History for U.S. Appl. No. 12/013,449, filed Jan. 13, 2008. Inventor: Joseph.

Extended European Search Report; PCT/US2010025119; Dated Jan. 21, 2013; 11 pages.

Johnson & Johnson Orthoplast Splinting Materials, http://www.medco-school.com/Supply/Product.asp?Leaf_Id-80365, archived 2007.

Aquaplast Splinting Materials, http://www.wisdomking.com/aquaplast-splinting, archived 2008.

* cited by examiner

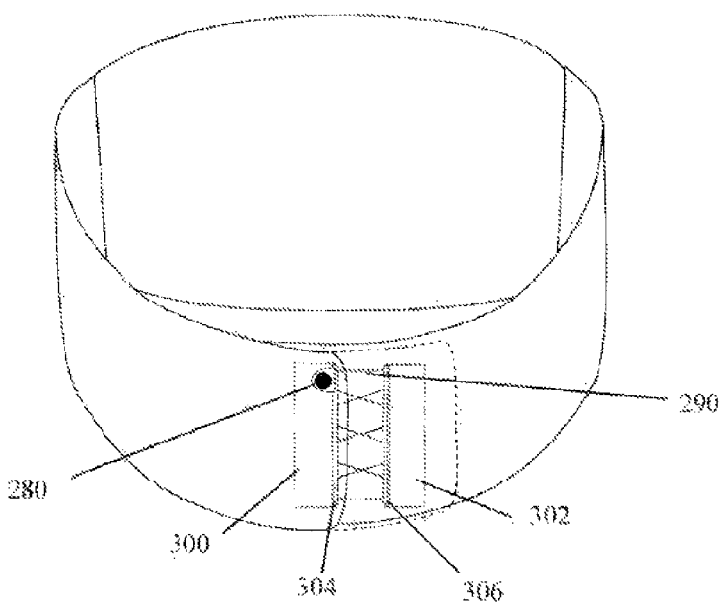
Figure 72
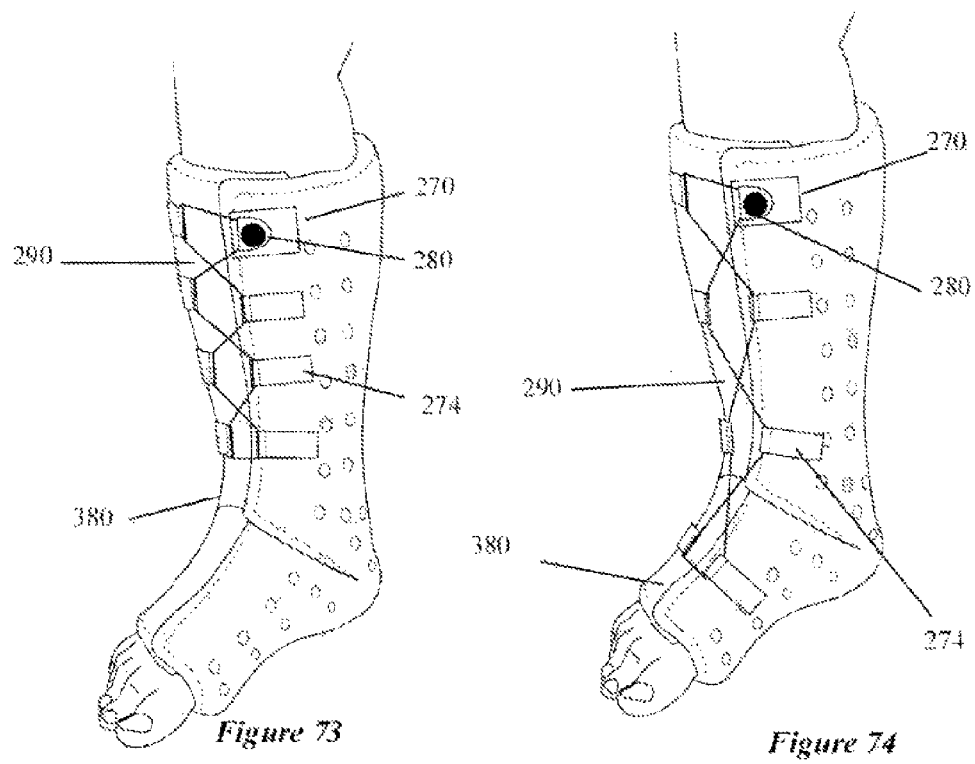
Figure 73
Figure 74

COMPOSITE MATERIAL FOR CUSTOM FITTED PRODUCTS

This application is a continuation of PCT/US2010/025119, filed Feb. 23, 2010, which PCT/US2010/025119 claims priority to U.S. Provisional Patent Application No. 61/155,138, filed Feb. 24, 2009, which PCT/2010/025119 is an international application of U.S. patent application Ser. No. 12/710,252, filed Feb. 22, 2010, which claims priority to U.S. Provisional Patent Application No. 61/155,138, filed Feb. 24, 2009, which PCT/US2010/025119 is an international application of U.S. patent application Ser. No. 12/711,188, filed Feb. 23, 2010, which claims priority to U.S. Provisional Patent Application No. 61/155,138, filed Feb. 24, 2009, and which U.S. patent application Ser. No. 12/711,188 is a continuation-in-part of U.S. patent application Ser. No. 12/710,252, filed Feb. 22, 2010, which claims priority to U.S. Provisional Patent Application No. 61/155,138, filed Feb. 24, 2009, each of which is hereby incorporated by reference in its entirety.

BACKGROUND

1. Field of the Disclosure

This invention relates to the field of custom formed products and particularly to the field of composite materials for use in orthopedic products.

2. Description of Related Art

It is often necessary to form products into custom shapes and fits. One area where this is a particular problem is in the use of protective and musculoskeletal supportive devices such as those used in the medical orthopedic field, sports medicine, protective body gear, veterinary uses as well as other uses. These devices need to provide varied degrees of support and protection yet fit the body closely and comfortably. Items such as form fitting orthopedic casts, orthopedic braces, support devices used in sports medicine, immobilization and alignment devices used for radiation therapy, and supportive devices used in veterinary medicine, as well as protective body gear and other rigid fitted items can all benefit from improved construction techniques and materials.

Orthopedic casts and braces are typically formed on the body by wrapping a fiberglass strip impregnated with soft resin which is activated and hardened by water. They can also be formed from plaster and fabric layers which are activated by water. Polycaprolactone material, such as Orthoplast®, distributed by BSN Medical is also used for braces. This casting and splinting material is heated with hot water to the highest temperature comfortable on the skin, about 160 degrees Fahrenheit. These materials allow the cast or brace to be formed and made in situ about the patient's body part over layers of padding and stockinette. These prior materials have a limited amount of time that they are sufficiently heated to a temperature where 1) they are sufficiently malleable to be formed about the body and 2) the material does not burn the patient or practitioner.

Often casts, splints, braces and other products are required to be formed in complex shapes. For example, a thumb spica cast or splint is often needed for support for thumb injuries. These are difficult to custom form and fit to a particular user. They are often formed in pieces and attached to the splint or cast body which creates a weaker support. The fit is not always particularly comfortable which leads to compliance issues. Other body injuries may require relatively complex shapes which are difficult and expensive to achieve.

Braces in particular are difficult to form into custom shapes. Braces often need to be flexible in order to allow flexing of the body parts, such as knees, ankles, wrists and other movable body parts. At the same time, the brace needs to be rigid to prevent injury to a weakened body part. Thus, most prior braces are complex mechanical devices that are difficult to create and even more difficult to custom fit to the body.

Orthopedic products such as casts, splints, braces and protective gear as well as other products are not only difficult to form into complex shapes with conventional materials; they often do not fit the patient particularly well. Since these products are typically manufactured with mechanical mechanisms or attached together with connections such as hook and loop or adhesives, or are non-moldable, they are not able to be custom formed to the patient. This lack of custom fitting leads to discomfort which affects the compliance, use and effectiveness of the product.

SUMMARY

The invention provides a unique composite material that can be easily custom fitted to a body party, formed into complex shapes, yet is highly rigid and strong at room temperature. The flat composite sheet material is relatively thin and can be cut into shapes, heated and then sewn, to form into complex three-dimensional shapes. Then the finished product is able to be heated and comfortably formed on the body to precisely fit and support body parts.

A preferred embodiment provides a composite material that is formed of a middle layer of rigid polymer material that is heat formable at temperatures at about 200 degrees Fahrenheit. This layer is sandwiched between layers of highly elastic stretch fabric materials and/or foam layers. The resulting composite material can be heated until the middle layer is malleable while the outer layers provide heat insulation, stability for cutting, sewing and shaping, in addition to making the composite material more durable while it remains warm and pliable.

The fabric and foam layers also allow the heated material to easily pass through a sewing machine when hot and pliable and provide durability to the seams which plastic alone would not provide. These fabric layers may have stretch characteristics that allow for three dimensional molding of the middle layer yet the elasticity of the fabric keeps the soft heated item compressed and formed to the body while it cools and hardens. In addition, the elastic layers provide memory that plastic alone may not have so the item returns to it's original shape upon reheating to be fitted to the body again.

The composite material in a preferred embodiment may also include insulating foam layers on one or both sides or in place of or in addition to, one of the fabric sandwich layers. This foam enables the composite material to be easily handled while in its heated state and provides a protective comfort layer to the body when worn. This expands the temperature range for the heat formable materials that can be used because the relatively low density foam protects the hands and body from heat while sewing and while forming to the body. Also, the insulative properties expand the time during which the composite material is malleable thus allowing more time to sew seams and also to form the item to the body.

The composite material of a preferred embodiment of the present invention, after it has been sewn into a basic three dimensional shape, can be heated and formed into further complex shapes due to the malleability of the heated middle layer with the elasticity of the composite layers. The product may be sold for use in this basic shape. Alternatively, the product is pressed flat to save on storage and shipping size. Then, the finished product can be can be reheated by the consumer to temperatures above 140 degrees Fahrenheit to enable it to be stretched and form fitted closely about complex surfaces such as, but not limited to, the body.

The material can be stretched and formed about a surface without sagging out of shape because the stretch fabric and foam layers provide memory and retention forces. This easily and quickly provides a snug, close fit of the material about the surface. Once the material cools, it forms a rigid and supportive structure. The mid layer plastic material can be of varied thickness and hardness to provide the desired amount of support, protection and flex for the intended use.

The composite material of a preferred embodiment of the present invention in a preferred embodiment has a key feature in that, unlike many rigid materials, it can be heated to a pliable state and sewn with a standard sewing machine to make low profile, stretch, complex, comfortable and attractive seams much as a normal stretch fabric garment is sewn. The fabric and/or foam layers cause the heated composite to behave much as normal stretch fabric would and allow the material to be machine or hand manipulated through the sewing machine in a normal manner.

The insulative properties of the outer foam layers extend the time the material stays warm and pliable so there is enough time to sew long seams and complicated stitching while protecting the hands from excess heat. The product can be reheated any number of times to complete the sewing, shaping and manufacturing process. In addition the composite material parts can be stretched differentially as they are sewn and manipulated to make high degrees of shape into the item as it is sewn. This enables three dimensional products to be easily made that were previously very difficult if not impossible to sew with cool rigid material parts. Upon cooling, the middle support layer material becomes rigid and is further reinforced by the three dimensional shape to become very strong and supportive. The sewn seams join the rigid pieces together in a continuous fashion which reduces point loading and fatigue found with other connection means such as rivets, adhesive or mechanical fasteners.

The fabric and foam layers of a preferred embodiment also provide comfort to the body as well as aesthetic appearance offered by printed or textured fabrics. The foam layer also provides cushioning to make the final fitted contoured product even more comfortable by eliminating pressure points during movement and when weight is applied. The foam layers may also be thermo-formable at the same temperatures as the middle polymer layer so they add additional shape and contour by changing thickness as pressure is applied during the molding process. These foam layers can be varied in thickness, density and composition to provide varied levels of cushioning as desired. This material composite and hot sewing technique combine to provide many desirable and unique features.

These and other features of the claimed inventions will be evident from the ensuing detailed description of preferred embodiments, from the claims and from the drawings.

BRIEF DESCRIPTION OF DRAWINGS

FIG. 72 is an illustration of the attachable closure mechanism in a different position on the brace.

FIG. 73 is an illustration of the attachable closure mechanism on a leg splint.

FIG. 74 is an illustration of the closure mechanism on a different position on the splint.

DETAILED DESCRIPTION OF PREFERRED EMBODIMENTS

Figure 1:
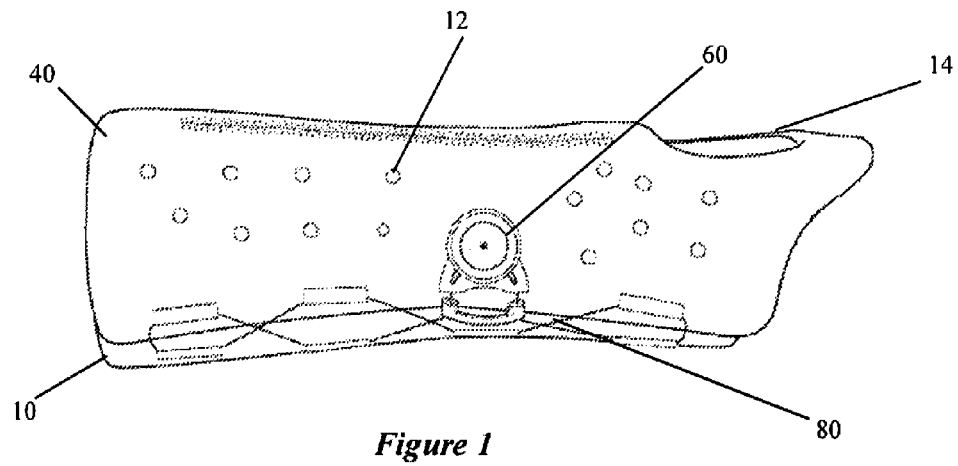
FIG. 1 is an illustration of an orthopedic brace formed from the composite material of a preferred embodiment of the present invention.

A preferred embodiment of the present invention is illustrated in FIGS. 1-74. It is to be expressly understood that the descriptive embodiments are provided herein for explanatory purposes only and are not meant to unduly limit the claimed inventions. The exemplary embodiments describe the present inventions in terms of orthopedic products used for immobilizing and supporting body parts. It is to be understood that the present invention is intended for use with other types of products, including without limitation medical, sports, protective gear, veterinary and other types of uses.

The following terms are defined herein as follows. A brace is a device used to assist or restrict body movement. A cast is a protective shell of material molded to protect a broken bone or fractured limb as it heals. A splint is a medical device for immobilizing or stabilizing an injured bone, joint, limb, or spine. An orthoses is an external orthopedic appliance used to support, assist, align, prevent or correct a deformity or improve function of a movable part of the body. Dwell time is defined as the time at which the composite material is sufficiently malleable to allow the product to be formed. The Target Temperature is defined as between about 165 degrees Fahrenheit and 250 degrees Fahrenheit, and preferably about 200 degrees Fahrenheit. For purposes of the present invention malleable is defined as a state at which the material becomes formable to three dimensional shapes by becoming bendable, highly stretchable in four directions and compressible to form complex shapes around body parts and other objects. A material that becomes slightly more formable and bendable yet does not have a high degree of the above features is considered not malleable. For purposes of the present invention, burning of human skin is defined as the material achieving such a degree of heat transfer when heated to 200 to 220 degrees Fahrenheit or above that painful discomfort prevents handling readily with the hands and painful reddening and or blistering of body skin results if the heated material is applied to the body.

Overview

Figure 2:
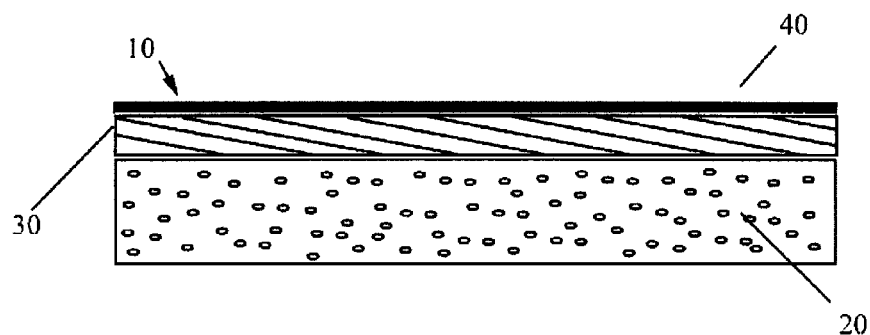
FIG. 2 is a side cutaway view of the composite material of FIG. 1.
Figure 3:
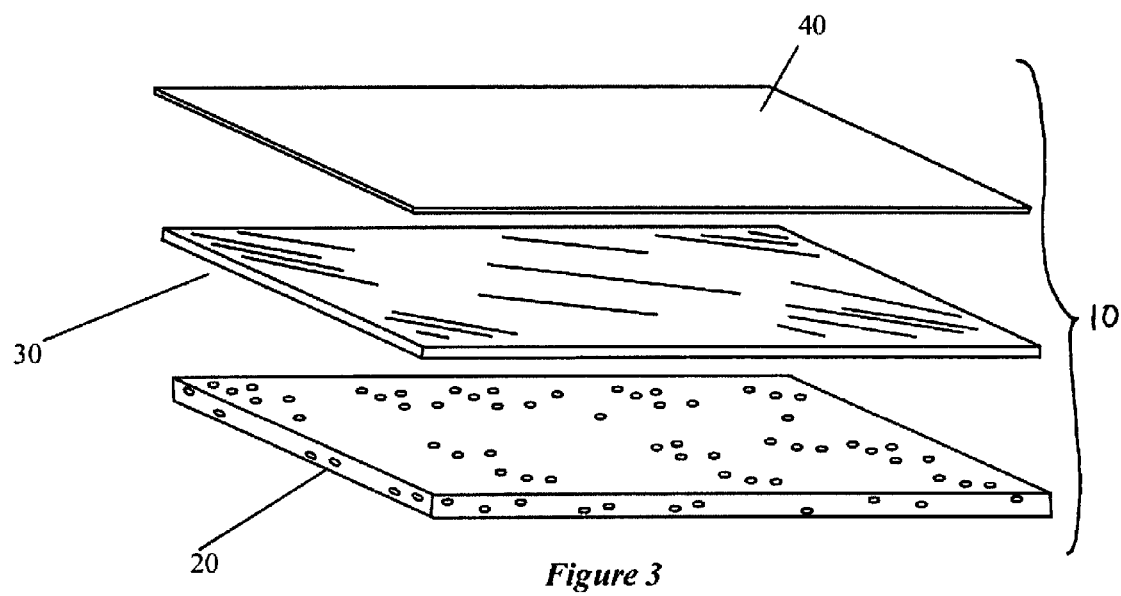
FIG. 3 is an exploded assembly view of the composite material of FIG. 1.

An example of an orthopedic product, such as a short arm fracture brace is illustrated in FIG. 1, on which the claimed invention may be used. It is to be expressly understood that other types of products, including other types of braces, splints, casts and other products. The descriptive brace 10 of this embodiment includes an inner layer 20, a middle support layer 30 and an outer layer 40 as shown in FIGS. 2 and 3. The three layers each provide unique functions and when combined into a unitized composite product that creates a unique and superior product. The three layers, each described in greater detail below, are molded or laminated together to form a unitized composite material. Closures 60 are applied prior to use that enable a health care provider without specialized training to easily form the brace in an appropriate shape and secure the brace to the patient. The resulting brace is much more comfortable for the patient and can increase the patient's compliance with its use. The resulting brace has many additional benefits over the previous systems as discussed above and below.

The unitized system of this preferred embodiment enables the brace to be provided in pre-laminated, pre-shaped or in blank sheets and provided in sizes according to a desired use, such as for supporting a wrist, arm, knee, neck or other body location. The system is then easily customized to the particular patient as discussed below. The system, in a preferred embodiment, also allows the brace to be adjusted as necessary by the patient to accommodate swelling or other issues. This adjustability also allows the brace to be customized to the particular body part being supported.

The brace system is heated with dry heat to become thermoformable for shaping within a few minutes. The brace system, at temperatures between 160 degrees Fahrenheit to 250 degrees Fahrenheit (the Target Temperature), is pliable for ease in shaping but still is able to maintain some degree of stiffness so not to be overly fluid, that is beyond the glass transition temperature of the material. The system can then be placed on the patient without burning or causing discomfort to the patient during this process. The relatively low density foam inner layer insulates the high density hot middle plastic layer from the body. The skin, having a higher density than the foam, actually cools the foam more rapidly than the foam can transfer heat to the skin thus protecting it from burning at the temperatures used. The system is then formed to the exact shape desired for that particular patient easily and without the need of specialized skill using a method described below.

The system of a preferred embodiment is designed to allow the time during which the brace system is malleable to be controlled. This is referred to herein as the "dwell time" for the brace. This is a critical time in that it is the time that physician or technician has to precisely mold the brace onto the patient's body. This preferred embodiment controls the dwell time by the selection of the middle layer material, the density/thickness of the middle layer material, the temperature range at which the middle material is malleable and the insulative qualities of the inner and outer layers. In addition, dwell time can be adjusted by the user depending on the temperature the item is heated to, higher temperatures resulting in longer dwell times.

In this preferred embodiment, the dwell time is controlled by the initial temperature that the middle layer is heated, by the material choice for the middle layer, by the thickness and density of the middle layer, and by the insulative characteristics of the inner and outer layer. This preferred embodiment uses materials for the rigid middle layer that are malleable at temperatures at or around 200 degrees Fahrenheit and down to about 160 degrees Fahrenheit. The forming temperature range of these materials by themselves would not normally enable the material to be malleable for a sufficient time and would cause severe discomfort or injury to the patient. These materials by themselves would cool in a matter of seconds when removed from the heat source. The encapsulation in the low density insulating foam inner and outer layers is an important innovation that increases the dwell time and allows it to be varied by the above means while at the same time, insulating the patient for the dangerous heat of the inner layer.

The composite material for the products is radiolucent. This allows X-rays and other imaging procedures to be conducted on the patient without removal of the product. This saves considerable time and expense in order to check the status of the healing process.

The composite material is able to be formed into complex shapes by heating the material and shaping, sewing and otherwise manipulating the material while it is in a malleable shape, then allowing it to cool and retain its new shape in a rigid form.

The composite material may also be created in a "blank" form and then formed in situ to create a desired shape and custom fit. This allows flexibility and customization without a large inventory of products.

Materials

The composite of this preferred embodiment includes a soft inner foam layer 20 assembled by laminating or molding or other manufacturing processes to the middle support layer 30. The inner foam layer 20 provides comfort next to the skin. It can protect the patient's skin from abrasion and heat from the middle layer 30 as well as being water proof (non absorbent). This layer may be formable at the Target Temperatures to provide a precise fit to the smallest details of the patient. The particular foam composition for this layer is low density as discussed above to dissipate heat so the patient is not harmed when the warm brace is initially placed around the body part. In other preferred embodiments, the foam may not be malleable but is able to compress to comfortably fit closely around the body part of the patient. The foam provides cushioning as well to increase the comfort and compliance of use.

The foam in the preferred embodiment is of a closed cell construction though alternatives may be open cell to provide breath-ability if waterproof features are not desired. This layer may also be of a foam formulation to accept and dispense therapeutic chemical additives such as antimicrobials, skin lotions or other medicines and chemicals. In addition, visco-elastic memory foam may be used for this layer to conform precisely to the body.

The inner layer 20, in this preferred embodiment, may include without limitation, materials such as a closed cell foam layer, an open cell foam layer, a gel or soft polymer layer, an insulating fabric, a multilayer or lofted insulating fabric layer, or any other cushioned insulative layer. This layer provides cushioning for comfort to the patient, along with insulative characteristics for maintaining the heat of the middle layer to increase the working time for shaping the material as well as providing a support surface for sewing operations. This support surface provides a securing mechanism for the threads of the sewing seam as well as providing a smooth surface for moving the heated composite material through the sewing apparatus without sticking. In addition, this layer insulates the heated malleable composite material from the base of the sewing apparatus to keep it malleable long enough to conduct complicated sewing steps. The base of most sewing apparatus are typically a large thick metal surface that will quickly sink heat away from an un-insulated material in a few seconds. The sliding coefficient of friction of this layer is about 1 or less when heated to a temperature of about 200 degrees Fahrenheit, meaning that it will slide across a metallic surface without undue force or stickiness.

This inner layer 20 in the preferred embodiment is formed from a foam material, such as from a variety of cross-linked Polyethylene ("PE") and Ethylene Vinyl Acetate ("EVA") foams or other suitable materials. The material is moldable at the Target Temperatures. However, this layer may also be moldable at higher temperatures about 300 degrees Fahrenheit which are achieved in the manufacturing process. This allows the material to be compression molded into various forms during manufacturing and for the edges to be heat sealed closed to the outer layer thus encapsulating the mid layer. This layer can be treated with various medicines or antimicrobial treatments.

An additional layer may also be affixed inside of the inner layer to provide antimicrobial features. Other therapeutic properties may be incorporated as well into these additional layers. This layer could be foam, fabric, non-woven fabric or other suitable material The middle layer 30 of this preferred embodiment is a thin thermoformable polymer plastic material that becomes pliable at the Target Temperature yet substantially rigid at room temperature. This layer provides a substantial amount of support for the body part. It may be engineered to have varying degrees of flexibility and rigidity as desired by varying the polymer material composition. The features may also be varied by the material thickness or by perforations or cut-outs. This layer may be molded with varied thicknesses, tapered edges, ribbing, holes and features that provide the desired rigidity, strength and flexibility required for the intended healing purpose.

The middle layer 30 of the preferred embodiment is formed from a proprietary thermoplastic polymer material that includes specific characteristics. The material is easily formable at temperatures between about 165 degrees Fahrenheit and 200 degrees Fahrenheit, and rigid at temperatures below 130 degrees Fahrenheit. The material preferably has a low glass transition temperature as well which will allow it to become slowly rigid from the malleable state. The material thickness ranges preferably within the range of about 0.025 inch to about 0.125 inch. This material has a hardness greater than Shore 7OA, and preferably within a range from about Shore 65D to about 80D when measured in accordance with ASTM D2240. The material has adequate structural strength with high impact strength, low notch propagation and durability. For example, and without limitation, the material of the preferred embodiment has a tensile strength in the range of 6000-9000 psi (ASTM D638), and preferably 7500 psi, elongation at break of 5% (ASTM D638) and a flexural modulus of between 270,000-340,000 psi and preferably 308,000 psi (ASTM D5023). The specific gravity of the preferred material is between about 1-1.5 grams per cubic centimeter (ASTM D79).

The middle layer 30 of another preferred embodiment is preferably formed from Polyvinyl Chloride ("PVC") sheet, Amorphous Polyethylene Terephthalate ("APET"), Recycled Polyethylene Terephthalate ("RPET") or PVC foam such as Sintra™ or Komatex™. Other preferred materials include without limitation polycaprolactone, and caprilactone. Also such materials as Low or High Density Polyethylene ("HDPE") and similar materials may be used as well. Additional materials that are thermoformable at temperatures below 250 degrees Fahrenheit while rigid at room temperatures may be used as well.

The outer layer 40, in a preferred embodiment, is formed from a stretchable material that will easily stretch, maintain memory to return to their original shape and posses high strength and durability characteristics. The material includes but is not limited to knit nylon spandex blend, knit polyester spandex blend, fabrics of nylon, polyester or other fibers that stretch due to the design of the knit, and rubberized materials. Spandex is the generic term for a highly elastic synthetic fiber. The preferred material in one embodiment includes a blend of nylon or polyester with spandex. Also, the preferred material for this embodiment does not become tacky when heated to temperatures above 200 degrees Fahrenheit and glides easily across surfaces when heated at that temperature. The sliding coefficient of friction of this layer is about 1 or less when heated to a temperature of about 200 degrees Fahrenheit, meaning that it will slide across a metallic surface without undue force or stickiness.

The outer layer, in another preferred embodiment, includes the stretchable material described above along with another foam layer that, in a preferred embodiment, has many of the features of the inner layer including providing insulation against the heat of the middle layer when forming the brace about a body part. Additionally it provides aesthetics to the brace and also provides protection from abrasion from the middle layer. It is intended to provide a durable and comfortable covering to the rigid and perhaps rough perforated middle layer. In this preferred embodiment, the outer layer is formed from a foam, such as urethane foam, foam rubber or EVA foam that is moldable at a temperature above the Target Temperatures. This allows the outer layer to be thermoformed during manufacturing with relief features, ribs, depressions or cosmetic shapes and to have the edges sealed to the inner layer at temperatures considerably higher than the Target Temperatures. Such features would not be affected during the patient forming process. The outer layer, in the preferred embodiment, does not thermoform at the Target Temperature, but will stretch to follow the shape of the mid layer. Since it does not thermoform, it will not pick up the imprint of the elastic wrap or compression tube and will remain smooth and attractive in appearance. It can be thermoformable at the Target Temperature if these features are not desired.

The outer foam layer may also be of a stiff foam to provide additional support, as well as environmental protection, aesthetics and also to provide some support during the thermoforming process. When comparing this outer layer with the typical abrasive plaster or fiberglass brace outer surface, significant improvements in comfort, appearance, aesthetics, durability and ease of use can be experienced. Also, fabric, synthetic leather or other cosmetic covering may be laminated to the outside of this layer for purposes of aesthetics or durability. In addition, fabric can be applied known as unbroken loop which has a surface compatible with common hook and loop fasteners such as Velcro™. This allows closures, extra supports, multipart braces and other devices to be instantly connected using common hook strip fasteners.

The composite material may include holes perforated through the three layers to form holes 12 in various amounts and shapes to provide ventilation, forming features, access to wounds or access to catheters etc. These apertures also allow the middle layer to expand and shrink as necessary as the brace is being molded to the body part. The unitized brace may also be perforated to create apertures 14 for body parts such as thumbs, toes, etc. It may also be perforated to accept various closure system attachments. In most cases, the preferred embodiment is wrapped once around the extremity and overlapped to some degree. This is to accommodate the varied body diameters and shapes encountered within each sized product and is a feature not found with typical plaster and fiberglass braces. The overlap is also the spot where the closure devices will be placed that allow the brace to be opened or closed in circumference during use.

Alternative Material Embodiments

The middle support layer may include perforations as well. This allows the layer to be easily conformable to the three dimensional surfaces of the body is to perforate it with small holes close together resulting in an open structure from 25% to 50% open. This method creates a matrix framework around the holes that, when heated and pliable, can more easily form by deforming around the small holes moving into the small holes or stretching the small holes apart. With this perforation method, thicker stiffer materials can be used than would not normally be adequately formable without the perforations. Perforating also allows the plastic polymer to be formed at lower temperatures than a continuous layer due to deforming process mentioned above which is important for patient comfort and safety. The thick matrix framework when cool and formed in a cylindrical fashion becomes very rigid as needed for the most supportive braces. In addition, weight is reduced by the perforations which increases the comfort and compliance of the patient. These perforations to the middle layer are separate from the ventilation holes that are used for ventilation and cooling purposes which must be punched through all of the layers and are intended to be larger and further apart. In a preferred embodiment of the present invention, the perforations remove between twenty-five to sixty percent of the weight of the middle layer. These perforations are particularly useful when the material for the middle layer includes PVC sheet, APET and RPET.

Alternatively, foam materials, such as PVC foam (including Sintra™ and Komatex™) and APET may be foamed when extruded or molded with 20 to 50 percent air or gas bubbles instead of perforations. Other foamed materials may be used such as rigid EVA foams and other high density foamed polymers. Their use depends on the desired rigidity and durability required for each use.

The middle layer 30 may have a varying topography such as by having increased thicknesses in areas where additional rigidity is desired and decreased thicknesses in areas where more flexibility is needed. In another preferred embodiment of the present invention, the entire brace system is formed from a single material and behaves in much the same manner as described for the multi layer brace above. This material would have strata that are more and less dense by incorporating more or less gas bubbles into a foam material. The center portion of the material has a higher density (less or no gas bubbles) than the outer portions of the material (more gas bubbles). This can be accomplished by using a foam extruded material where the foam is crushed or manipulated during the manufacturing process so it becomes more dense. It is then processed with heat or other means so the surface lofts and the gas bubbles expand and becomes less dense and more cushioned. This could also be achieved by co-extruding or co-molding multiple layers at the same time which could be foamed to different densities or using different compositions of materials co-extruded. The net effect is a single material sheet with a stiff center portion and cushioning, insulating outer portions. The lower density (more foamed) outer portions of the material can then insulate the inner portion during the forming process about the body part protecting it from discomfort from the heat of the inner portion. This insulation also provides sufficient dwell time for the brace to be formed about the body part extending the time the center portion is pliable. Additional layers can be added as well to provide additional therapeutic and aesthetic benefits.

The middle layer may also include multiple layers of heat formable material. These different materials may include different characteristics of rigidity and heat formability, or they may only be on certain areas of the middle layer to increase rigidity or flexibility at certain areas of the middle layer. Also, additional materials may be inserted in the middle layer at desired locations to provide additional rigidity or flexibility as needed. Manufacture The manufacturing process of a preferred embodiment uses a heat press process. The three component layers are placed in the appropriate mold or die, depending on the particular product being formed. The mold/die with the three (or more) layers in place is then placed into a convection oven and heated to 300 degrees Fahrenheit. The heated mold/die is then placed into a press. The press is closed so that the three layers are compressed into the mold shape. The press remains closed until the three layers have cooled sufficiently to retain their shape. Once the composite material has sufficiently cooled, the molded composite material product is ejected from the mold. Other finishing steps may be taken to complete the product, such as forming holes, attaching closure mechanisms, etc.

Figure 4:
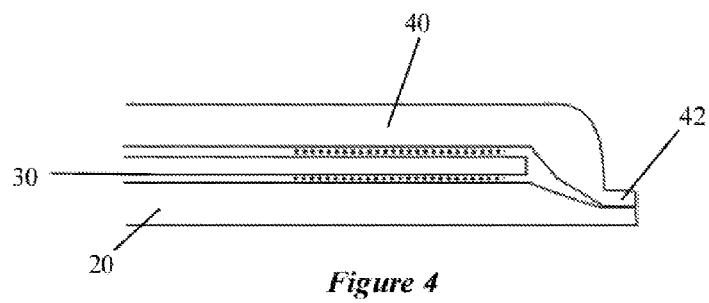
FIG. 4 is a side cutaway view of the composite material with rounded edge.

Another manufacturing process also uses a molding process. The middle layer 30 is sandwiched between the inner layers 20 and outer layer 40 and recessed from the edges of those layers during the molding process. In this process, the layers are all heated above the Target Temperature. The mold includes a cut-off line on its outer edge to cut the foam of the inner layer 20 and outer layer 40 as well as any fabric layers. In addition, next to the cut-off line a bar compresses the layers to a high degree. The edges of those layers are pinched to seal the edges of the product and tightly closed permanently bonding all layers in the molding process. This provides a clean, soft, rounded thin edge 42 to the brace as shown in FIG. 4 that is durable, comfortable and less prone to abrade the skin which is a common problem with traditional plaster and fiberglass braces.

Alternatively, the edges may be sealed with an edge tape on the exposed edges. This allows the brace to be formed in blank sheets and custom cut for a particular purpose. The edge tape seals the exposed edges and also forms a soft edge. This tape can be of a flexible thin fabric or foam with an adhesive backing that is easily applied by hand to edges of the brace where desired.

Another manufacturing process is compression molding which typically includes the following steps. Fabric layers, if used, are laminated to the inner and/or outer layers. Blanks and features are then die cut out of each layer. The middle layer is put inside the inner and outer layers set back from the edges. The three layers are heated to the critical molding temperature which is above the Target Temperature. The heated layers are placed in a compression mold where the layers are compressed to cut features in the layers and edges are sealed by a compression bar. The layers are cooled by the mold to form the composite material.

This embodiment does not require lamination as the parts are molded together. However, this embodiment may also include the layers 20, 30 and 40 laminated together. The outer layers extend beyond the middle layer to form a soft edge 42. The edges of the outer layers may be laminated, laminated and molded or molded with heat sealed edges and spot adhesive.

It is to be expressly understood that other lamination or manufacturing processes can be used as well, such as the use of hot adhesives, sewing or any other method of assembling the layers together.

Closure Systems

A closure system 60 is used to secure the product closed about the body part as shown in and to allow some degree of compression to hold the injury in reduction. This system may be double sided adhesive tape placed in between the overlap, adhesive tape applied to the seam or circumferentially, or a mechanical closure system. These mechanical closures may consist of, but are not limited to, hook and loop fastener, snaps, laces, toothed zip ties, ratchet lace systems, ski boot type buckles and the like. In a preferred embodiment, the closure system can be fastened and the tension adjusted by the attending doctor or technician as the brace is applied with a tamper proof closure so it cannot be adjusted by the patient. It can be later readjusted by the attending doctor or technician by means of a tool to access the tamper proof adjustable closure. If desired by the attending doctor or technician, the closure could be set so the patient has the means to only loosen or tighten the brace a limited amount but it cannot be prematurely removed. This allows the patient to loosen the brace if there is discomfort or swelling and tighten it if too loose without going back to the physician. In addition, the system could be set by the attending doctor or technician so the patient has the ability to adjust and completely remove the brace. This can extend the life of the brace so it can be used as a temporary brace to protect the partially healed injury during rigorous use. Using this controllable and adjustable system, the attending doctor or technician has options appropriate for all phases of healing and can enable or lock out the patients ability to make adjustments.

Figure 5:
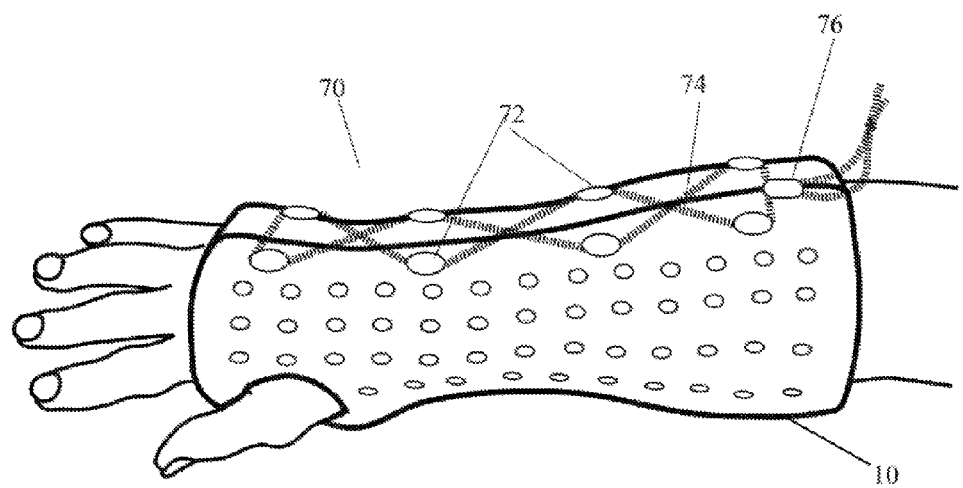
FIG. 5 is an illustration of an orthopedic brace formed from the composite material mounted on an arm.
Figure 6:
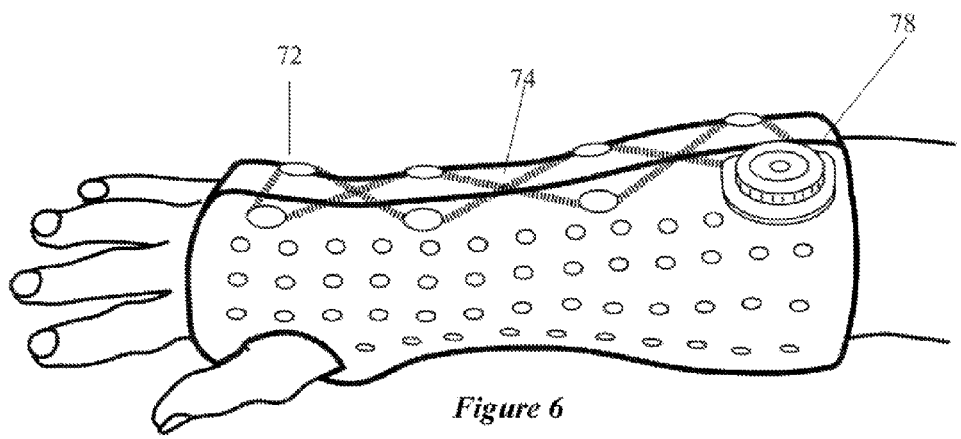
FIG. 6 is an illustration of the brace with a different closure mechanism.

One attachment mechanism in particular includes a tensioning cable system 70 as shown in FIG. 5. The system 70 utilizes a series of guide members 72 on opposite sides of the brace system 10. Lace 74 is laced through guide members 72 on alternate sides as shown in FIG. 5 and then through locking member 76. The lace is drawn tight so the brace has the appropriate tension on the body part and locked into place. An alternative lacing system shown in FIG. 6 is similar to the above mechanism but utilizes a reel mechanism 78 to mechanically tighten and lock the tightened lace that can be easily released and tightened with micro adjustments. In this embodiment, the fastening mechanism 60 include cable reel elements such as the cable reel attachment systems distributed by BOA Technology Inc. and described in U.S. Pat. Nos. 6,289,558; 6,202,953, 5,934,599, 7,591,050, 7,950,112, 7,954,204, 7,992,261, 8,091,182, and 8,277,401, all incorporated herein by reference; and U.S. Published Patent Applications 20080060167, 20060156517 and 20020095750 all incorporated herein by reference. The cable reel 78 can rotate to tighten the lace and may be pulled vertically to release the lace. Other fastening mechanisms may be used as well including cord locks, cam cord locks, traditional lacing bows, ratchet lace systems, and other lacing methods. An alternative system using ski boot buckles such as ratchet strip buckles can also be used in a similar fashion with pieces of hook fabric at either end as described in greater detail below. These systems can have features mentioned in the above paragraph regarding the attending doctor or technician's ability to lock out patient access to adjustment or allow varied degrees of adjustability built into the mechanism.

Figure 7:
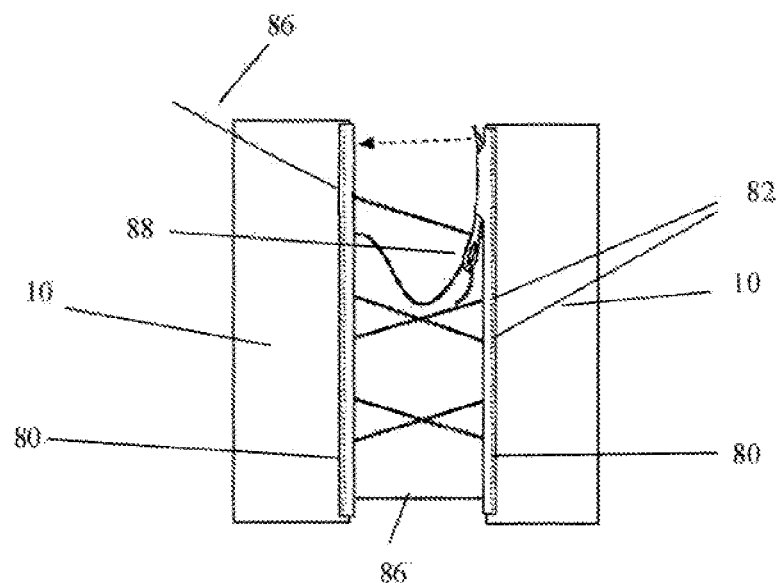
FIG. 7 is an illustration of a different closure mechanism.

Another present invention provides a unique lacing system. The lacing system shown in FIG. 7, provides an edging 80 along the edges of the cast, brace, or any other product. The edging 80 includes a series of perforations 82 spaced vertically along the edging 80. The edging may be secured with hook and loop fasteners, sewn onto the product, adhesively mounted, or otherwise attached to the product. The bottom of the edging includes a hook and loop strap extending around the circumference of the product. Alternative mechanisms may be used as well such as strap and buckle or any other known attachment mechanism.

A monofilament line 86 is inserted through opposing sections of the perforations 82, by use of a needle or awl 88. The ends of the line 86 end at the end of the product adjacent the hook and loop strap. The ends are pulled to tighten the line so that the edges of the product are pulled together. Once the product is tight about the body part or other object, the line 86 is wrapped around the product and secured by the hook and loop strap. Cord locks or other mechanisms may also be used to secure the line as well. Cables, laces or other mechanisms may be used in lieu of the monofilament line as well under the present invention.

Figure 8:
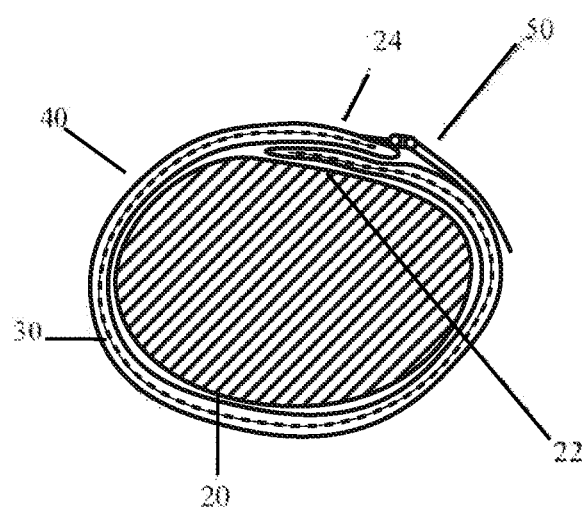
FIG. 8 is a front cutaway view showing the overlapped edges.
Figure 9:
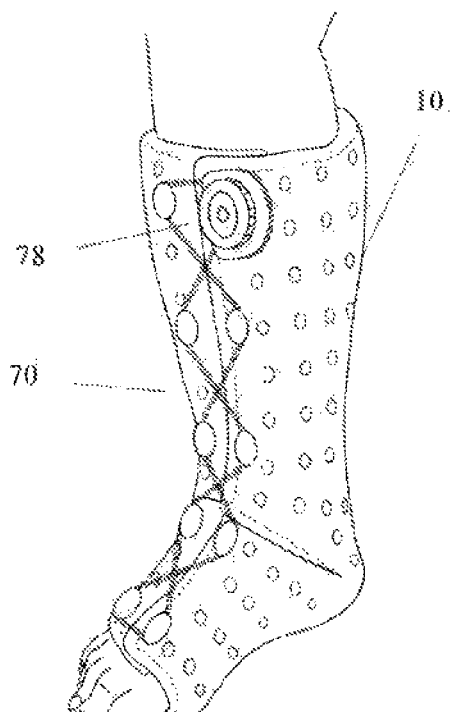
FIG. 9 is an illustration of a different orthopedic brace formed from the composite material.
Figure 10:
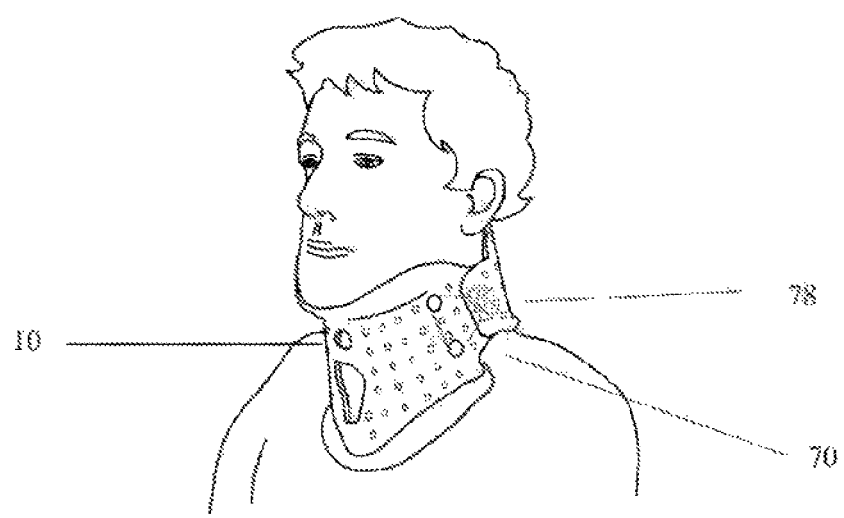
FIG. 10 is an illustration of a neck brace formed from the composite material.
Figure 11:
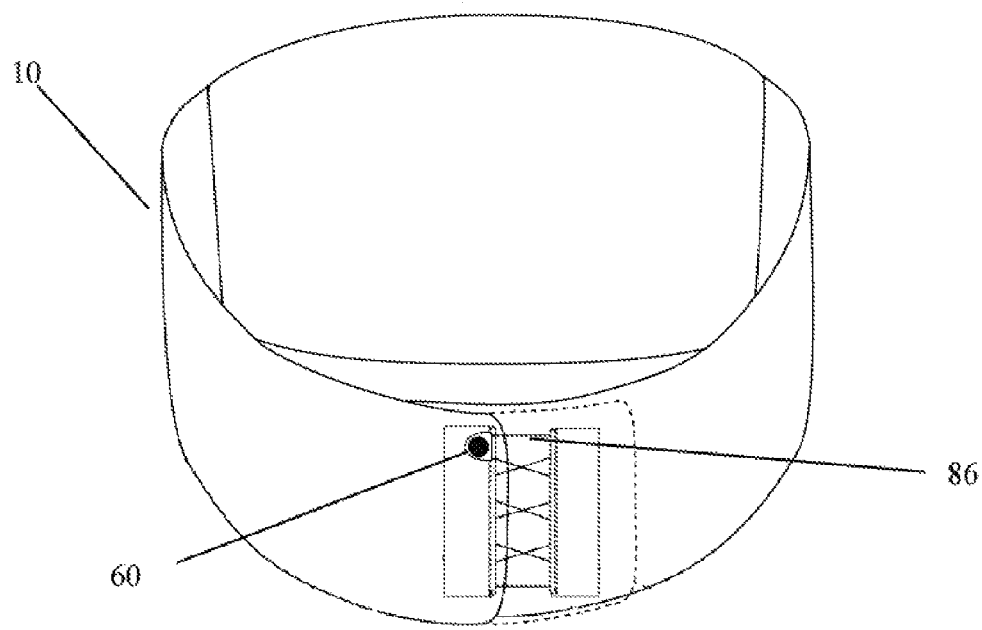
FIG. 11 is an illustration of a back brace formed from the composite material.
Figure 12:
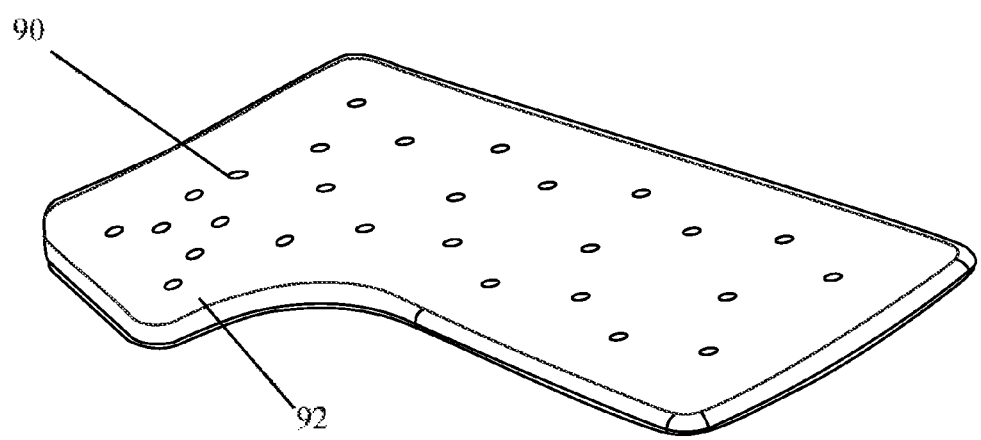
FIG. 12 is an illustration of a splint formed from the composite material.

The securing mechanism 50 of the brace system 10 of a preferred embodiment allow the edges of the brace system to overlap. This overlap amounts to about twenty-five percent (25%) of the circumference or less. The closure system discussed above is mounted on this overlap. This increases the adjustability of the brace system to increase or decrease the compressibility on the injured body part. The unitized brace system 10 may be provided in various sizes to fit different body parts and sizes of body parts. The adjustable overlap, as shown in FIG. 8 of the unitized brace system of this preferred embodiment provides further capability to custom fit the brace to a particular body part of a particular patient by allowing edge 22 of the brace to overlap the opposing edge 24. The securing mechanism 50 allows the brace to be adjusted by increasing or decreasing the amount of the overlap to more closely fit the patient's body part.

Applications Brace

The above unique combination of brace features provides a lightweight yet structurally rigid brace that is easily custom formed to the patient on site without the need for specialized training or skills. The resulting brace is patient compliant and can be adjusted as needed to increase compliance with its use. The adjustability can also decrease soft tissue injuries. The brace can be formed with dry heat so many heat sources can be used. The patient is protected from damage or discomfort from the heated brace during the forming process. The brace is waterproof and durable and can be reused and reshaped as needed. The materials used, being mostly polymers, provide a high degree of radiolucency. the body part can be examined through x-rays without the need to remove the brace as compared with Fiberglass and plaster which are not typically radiolucent. There is a reasonable potential for using recycled polymers in the construction of the middle layer that may impact the beverage container industry.

The unitized brace system of this preferred embodiment may be provided in a relatively flat shape or generally in the shape for a specific body part, such as a wrist, ankle, knee or other body part as well as in general sizes, such as large, medium, small. The braces may also be pre-formed in some cases to approximately fit the body part for trial of size or in the case where a more complex structure requires it. The system can then be heated and custom shaped to specifically fit the body part that it is to support. The adjustable overlap also contributes to this custom fitting as discussed above. The unitized brace system will then fit the body part in a comfortable yet rigid manner.

Examples of the preferred embodiments of the present invention used in types of braces are shown in FIGS. 1, 5, 6 and 9-11. This use is of particular advantage since this area of the body is particularly sensitive and the contour shape varies greatly from person to person. This use has advantages brought by the durable nature of the materials used since they are less prone to fatigue and cracking under body weight. In addition, the ability to adjust tension in this area prone to swelling is of great advantage.

The unitized brace system 10 can be thermoformed utilizing a dry heat source in lieu of typical water activated materials presently in use. One disadvantage of these typical materials is that the body part, and often wounds associated with the injury are wetted during the brace process. They typically remain wet many hours after brace causing the skin to become uncomfortable, abraded and more prone to build up of microorganisms at precisely the time when sterility is most desired. Examples of the preferred embodiments of the present invention stay dry during the brace process and provide only a brief and comfortable dry heating of the body part. Healing begins in a dry environment less prone to the buildup of microorganisms and infection. The use of antimicrobial treatments incorporated inside the brace can be more effective in this dry environment The brace system can also be shaped and secured to the body part without the need for extensive training since it is pre-made and not built on the patient. These pre-made braces have most of the labor done at the factory where they are manufactured saving valuable high cost hospital and clinic time adding considerable advantage. The brace system is also waterproof, lightweight and comfortable thus enhancing the patient's compliance in the use of the system. The polymer plastics used are much more durable than fiberglass or plaster and resist fatigue and cracking This combined with ability to adjust the tension and size of the brace or remold it can allow a single brace to be used throughout the healing process where typical braces are replaced 1-3 times upon repeated visits to the hospital or clinic.

The brace, when warm, soft and pliable must be formed to the intimate shapes of the body to best stabilize the injury under reduction. A loose fitting brace with voids between the body and brace can allow undesired movement. A perfectly formed brace that meets every detail of the body can provide stabilization without being excessively tight and in many cases, just meeting the body with out compressive force. This is the most comfortable configuration that will provide the needed support yet not constrict, reduce circulation or irritate. In order to achieve this desired effect, a unique method of forming this brace to the body must be incorporated. Since the overlap opening as shown in FIG. 8 that is formed from side edges 22, 24 of the brace is adjustable in circumference, this brace is best formed when warm and pliable by applying compressive circumferential force in excess of the comfortable level for long term wear. Once the brace is cool and rigid in a few moments, this compression can be removed and the closures can be adjusted to provide the desired amount of closure of the brace for comfort and stabilization.

Cast

A cast of the preferred embodiment is similar to the brace as described above. The primary difference, if any, is that the middle support layer is formed of a more rigid material. This can be accomplished by simply providing a material with greater thickness, or by selecting a material that has a higher durometer and tensile strength. The cast is applied by first heating the cast to the Target Temperature, applying it around the body part, and compressing the malleable material into the appropriate shape around the body. The lacing system can then be pulled tight to apply the appropriate amount of tension and to secure the cast. The tension on the cast can be adjusted to accommodate increase or decrease in swelling, itching or other issues. The cast of the composite material is waterproof so that the patient can bathe or shower with it on without the use of protection around the cast, and the patient may even swim with it. The cast is easily removable by loosening the tension in the lacing system so that a cast saw is not necessary.

Splint

The system, in a preferred embodiment, provides a unitized splinting system that is far superior to previous systems. The system of a preferred embodiment of the present invention, as used as a splint, is shown in FIGS. 12-17. This splint system is illustrated as a wrist splint but it is to be expressly understood that it can be used for any type of splinting situation, such as but not limited to foot splints, neck splints, leg splints, arm splints etc. This splint system 90 of this embodiment includes an inner comfort padding layer 20, a middle support layer 30 and an outer durable padding layer 40 as shown in FIG. 2. The three layers each provide unique functions and when combined into a unitized splint create a unique and superior splint. The three layers, each described in greater detail below, are molded or laminated together to form a unitized splint. The resulting splint is much more comfortable for the patient and can increase the patient's compliance with its use. The resulting splint has many additional benefits over the previous systems as discussed above and below. It is to be expressly understood that additional layers beyond the three layers described herein may be used as well.

The splint system of this preferred embodiment enables the splint to be pre-laminated, pre-shaped or in blank sheets and provided in sizes according to a desired use, such as for supporting a wrist, arm, knee, neck or other body location. The system is then easily customized to the particular patient as discussed below. The system, in a preferred embodiment, also allows the splint to adjusted as necessary by the patient to accommodate swelling or other issues. This adjustability also allows the splint to be customized to the particular body part being supported.

The splinting system is heated, preferably with dry heat (although hot water may be used as well), to become thermoformable for shaping within a few minutes. The splinting system of this preferred embodiment at temperatures between 160 degrees Fahrenheit to 250 degrees Fahrenheit (the Target Temperature) is pliable for ease in shaping but still is able to maintain some degree of stiffness so not to be overly fluid, as would be reached beyond the glass transition temperature of the material. Other Target Temperature ranges may be used as well with other materials. The system can then be placed on the patient without burning or causing discomfort to the patient during this process. The relatively low density foam inner layer insulates the high density hot middle plastic layer from the body. The skin, having a higher density than the foam, actually cools the foam more rapidly than the foam can transfer heat to the skin thus protecting it from burning at the temperatures used. This system which is preferably dry heated is then formed to the exact shape desired for that particular patient easily and without the need of specialized skill using a method described below.

Uses

Figure 13:
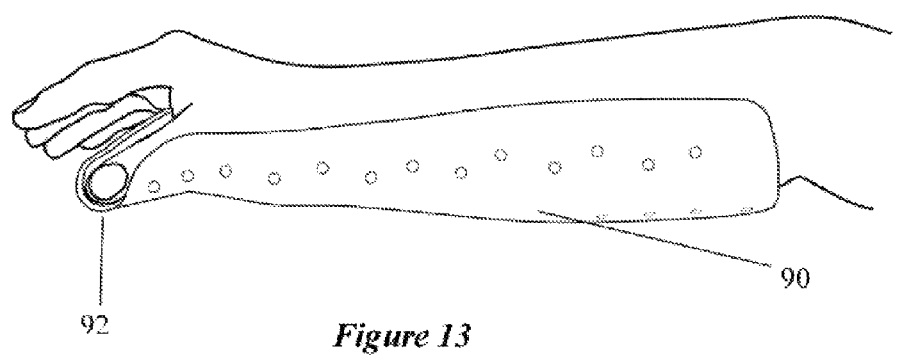
FIG. 13 is an illustration of the splint formed on a patient.

Examples of different types of splints are shown in FIGS. 12-17. The splint 90 in FIG. 12 has a flat custom shape for use in splinting an arm or wrist with an "L" shaped upper portion 92. Once the splint has been heated and molded (as described in greater detail below) the L shaped upper portion 92 is molded to comfortably support the wrist and thumb of the patient as shown in FIG. 13.

Figure 14:
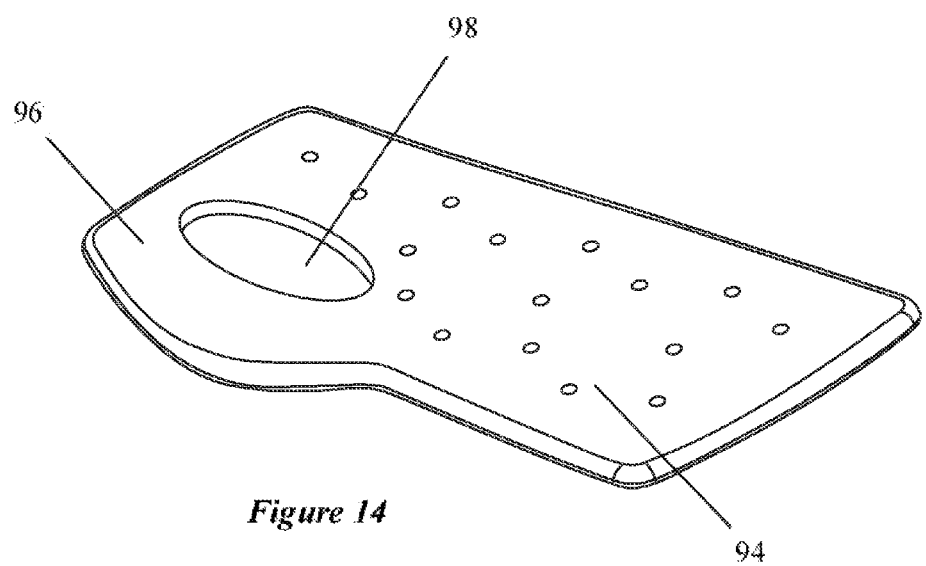
FIG. 14 is an illustration of another splint.
Figure 15:
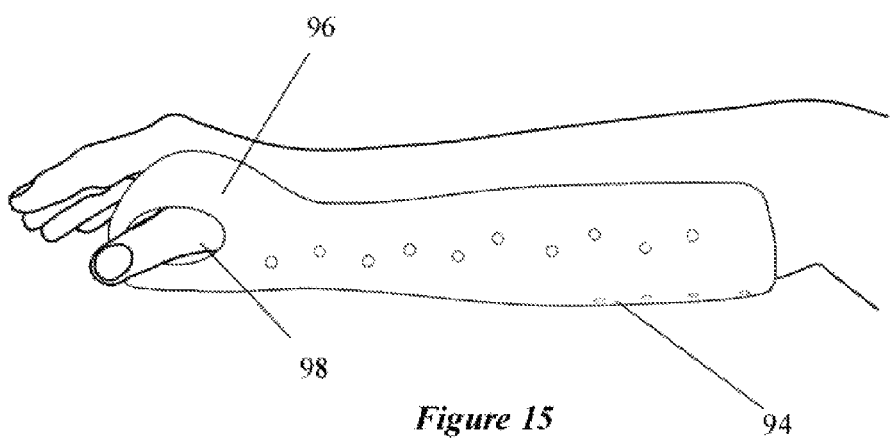
FIG. 15 is an illustration of the splint formed on a patient.

Another example of a splint for supporting a wrist or arm injury is shown in FIGS. 14, 15. The blank splint 94 includes a larger upper portion 96 with an aperture 98 formed in it. This splint is heated and molded to custom fit the patient with their thumb extending through the aperture 98.

Figure 16:
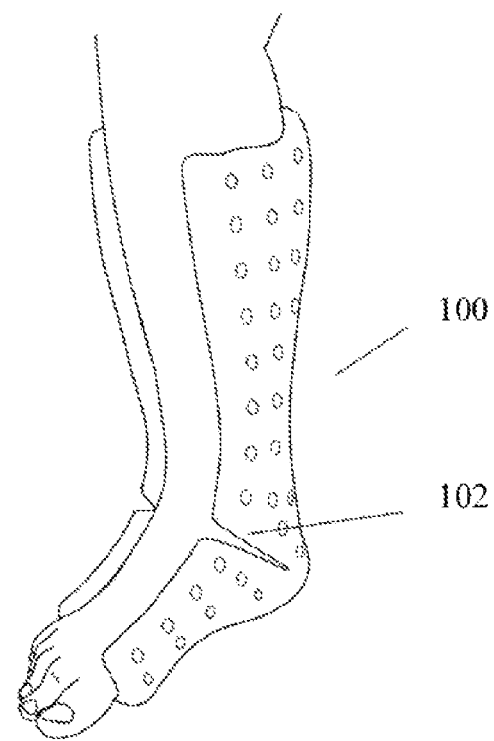
FIG. 16 is an illustration of a leg splint.

Another example of a splint of the preferred embodiment is illustrated in FIG. 16. This splint 100 is intended for use in splinting a leg injury. The splint includes slits 102 formed in each side of the lower portion of the splint which acts a hinge during the molding process so the lower portion of the splint can be pivoted to create a foot or boot portion on the splint.

Figure 17:
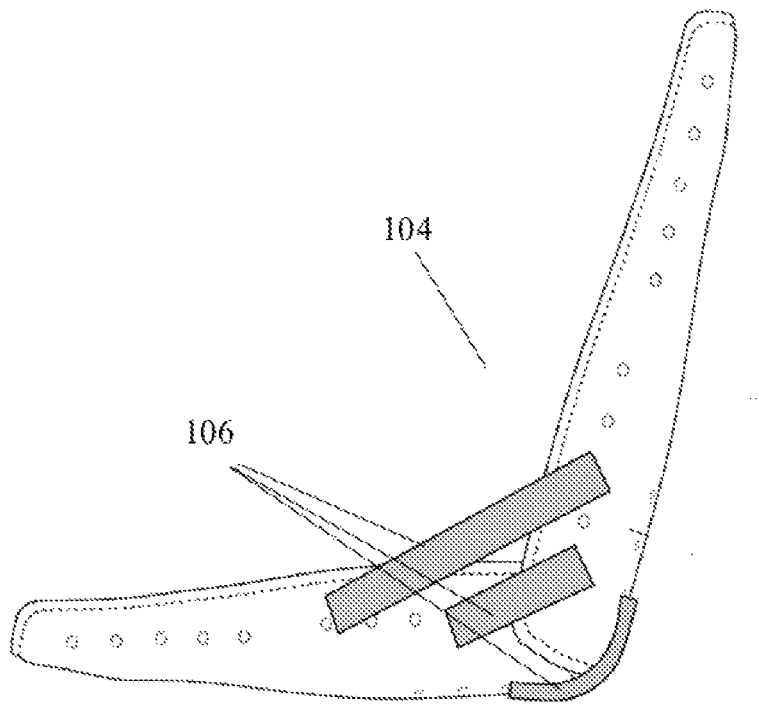
FIG. 17 is another illustration of a leg splint.

Another splint is shown in FIG. 17. This splint 104 has unbroken loop fabric laminated onto the outer surface 40. This enables two more sections of splints to be attached in a desired configuration to one another by sections of unbroken loop fabric 106. Thus, complex shapes can be created as needed in a quick and easy method.

Splint Application

The splint, when warm, soft and pliable must be formed to the intimate shapes of the body to best stabilize the injury under reduction. A loose fitting splint with voids between the body and splint can allow undesired movement. A perfectly formed splint that meets every detail of the body can provide stabilization without being excessively tight and in many cases, just meeting the body with out compressive force. This is the most comfortable configuration that will provide the needed support yet not constrict, reduce circulation or irritate. In order to achieve this desired effect, a unique method of forming this splint to the body must be incorporated. The splint is best formed when warm and pliable by applying compressive circumferential force in excess of the comfortable level for long term wear. The compressive force will cause the splint 10 to conform and shape. Once the splint is cool and rigid in a few moments, this compression can be lessened to provide the desired amount of tension of the splint for comfort and stabilization.

Figure 18:
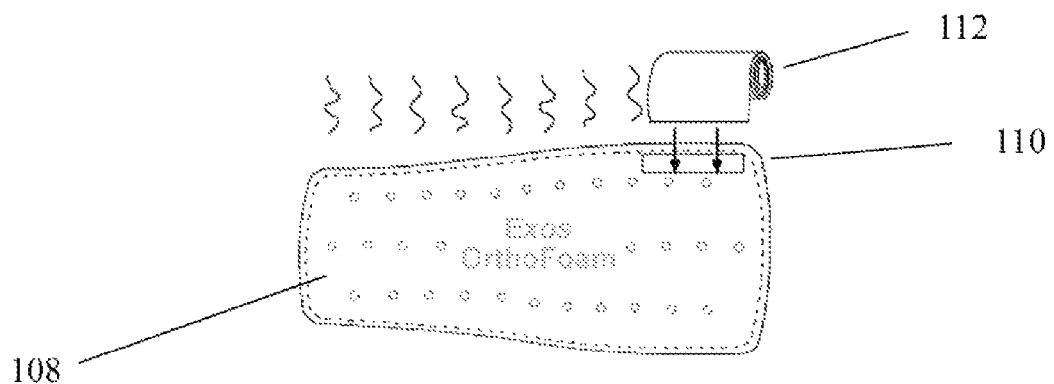
FIG. 18 is an illustration of a splint being prepared for use.
Figure 19:
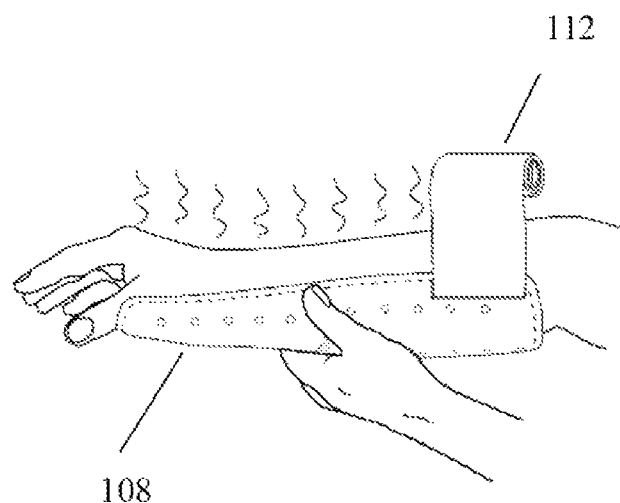
FIG. 19 is an illustration of the heated splint being formed on a patient.
Figure 20:
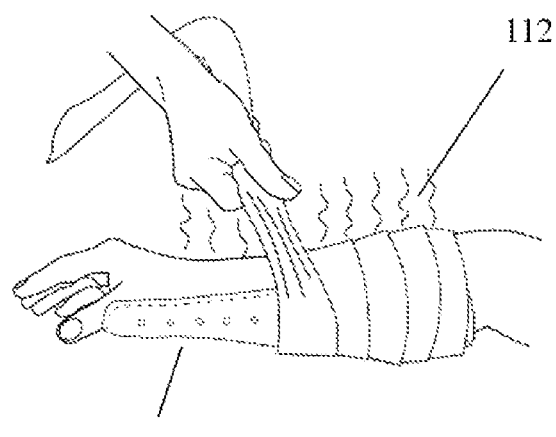
FIG. 20 is an illustration of the splint being compressed about the patient.

The preferred method of compression uses an elastic band 112 as shown in FIGS. 18-20 that can be quickly wrapped around the warm pliable splint as soon as it is installed. This elastic band may be fabric or rubberized material in the appropriate width, thickness and elasticity for the particular splint type in a length to adequately wrap over the entire splint. Compressive pressure can be varied simply by pulling on the band as it is wrapped. This process will insure that every part of the splint is formed to the body and voids are not created. It should be expressly understood that, though this process is commonly used to apply compressive pressure to wounds, it is a unique process to apply it to temporarily form a splint that is in a warm and pliable state for the duration of cooling, then to be removed.

In a preferred embodiment as shown in FIGS. 18, 19, a strip of hook fastener 110 is secured to the lower end of the splint 108 or the entire surface 40 can include unbroken loop fabric. The elastic band 112 can then be fastened to the element 110 to secure the band initially. The elastic band will naturally engage with the hook fastening elements. This allows many options for fastening the splint to the body or attaching multiple splint pieces together. This allows complex configurations to be formed.

Figure 21:
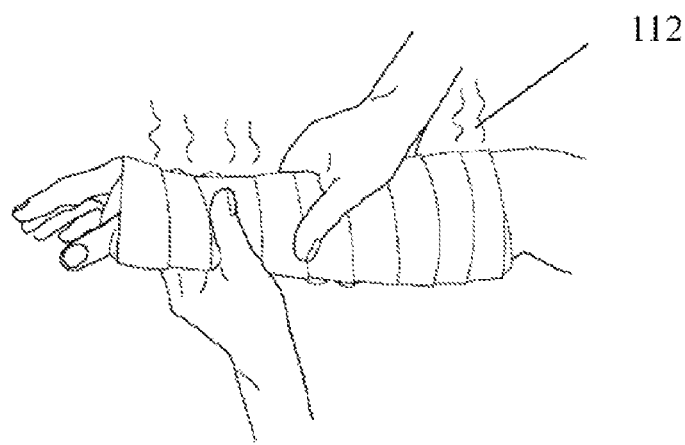
FIG. 21 is an illustration of the splint being molded about the patient.

The elastic band 112 is then wrapped snugly about the splint as shown in FIGS. 19, 20 so that the warm middle layer 30 conforms about the body, as shown in FIGS. 20, 21. The elastic band is then removed as the splint cools to form a rigid support structure.

The above unique combination of splint features provides a lightweight yet structurally rigid splint that is easily custom formed to the patient on site without the need for specialized training or skills. The splint can be formed with dry heat so many heat sources can be used. The patient is protected from damage or discomfort from the heated splint during the forming process. The splint is waterproof and durable and can be reused, reshaped and washed as needed. The materials used, being mostly polymers, provide a high degree of radiolucency. The body part can be examined through x-rays without the need to remove the brace as compared with fiberglass and plaster which are not typically radiolucent. There is a reasonable potential for using recycled polymers for some or all of the components which has an environmental advantage.

The unitized splinting system of this preferred embodiment may be provided in a relatively flat shape or generally in the shape for a specific body part, such as a wrist, ankle, knee or other body part as well as in general sizes, such as large, medium, small. The splints may also be pre-formed in some cases to approximately fit the body part for trial of size or in the case where a more complex structure requires it. The system can then be heated and custom shaped to specifically fit the body part that it is to support.

The unitized splinting system 10 can be thermoformed utilizing a dry heat source in lieu of typical water activated materials presently in use. One disadvantage of these typical materials is that the body part, and often wounds associated with the injury are wetted during the splinting process. They typically remain wet many hours after splinting causing the skin to become uncomfortable, abraded and more prone to build up of microorganisms at precisely the time when sterility is most desired. Examples of the preferred embodiments of the present invention stay dry during the splinting process and provide only a brief and comfortable dry heating of the body part. Healing begins in a dry environment less prone to the buildup of microorganisms and infection. The use of antimicrobial treatments incorporated inside the splint can be more effective in this dry environment The splinting system can also be shaped and secured to the body part without the need for extensive training since it is pre-made and not built on the patient. These pre-made splints have most of the labor done at the factory where they are manufactured saving valuable high cost hospital and clinic time adding considerable advantage. The splinting system is also waterproof, lightweight and comfortable thus enhancing the patient's compliance in the use of the system. The polymer plastics used are much more durable than fiberglass or plaster and resist fatigue and cracking.

Splint Use

In use, the unitized splinting system 10 is provided as a kit to the individual, the orthopedic specialist, physician, technician, first responder or other entity. The appropriate kit type and size for the body part to be supported is selected. A dry heat source, as discussed below is applied to the splint 10 until the splint is sufficiently pliable to allow it to be shaped. This should be in the range 160 F to 300 F (Target Temperatures) and preferably 200 F. In the preferred embodiment, the temperature of the splint is maintained at the desired temperature, such as 200 F for about five to ten minutes. The dry heat source can be an oven, microwave, or as discussed below, a heat bag, an internal heating mechanism or an exothermic heat source Once the splint is sufficiently heated and pliable, approximately 5-10 minutes, it is removed from the heat source and the elastic bandage is affixed to the splint.

The splint is then applied directly to the body part as shown in FIGS. 18-21. The lower density polymer foam that makes up the inner layer 20 dissipates the heat so that that the individual does not suffer any pain or discomfort from the heat. The splint will be pliable, in the preferred embodiment, for about three to ten minutes. This allows ample time to form the splint about the body part. An elastic wrap 112 is utilized to provide compression to mold entire splint specifically to the body part as shown in FIGS. 18-21. The elastic wrap 90 applies pressure uniformly over the splint 10. The elastic wrap 90 can be an elastic band, or an elastic compression bandage formed from nylon/tricot knit, rubber, urethane, spandex or any other suitable material.

The injury may be reduced or aligned during the forming process as well. The dwell time of the splint should be sufficient to allow the forming and reduction to occur.

The combination of the pliable heated thermoformable layers along with the uniform pressure forms the splint to the body part. The mid layer provides the majority of the shape and support. The inner layer, if formed of a thermoformable material will also shape to conform about the body part as well. The outer layer, in the preferred embodiment, does not thermoform, but will stretch to follow the shape of the mid layer. Since it does not thermoform, it will not pick up the imprint of the elastic wrap and will remain smooth and attractive in appearance. This layer can be thermoformable at the Target Temperature if these features are not desired.

Veterinary

The composite material also has particularly utility for veterinary use, particularly with equines. It is difficult to provide immobilizing supports to large animals such as horses as well as other domestic and wildlife animals. The composite material as described above is lightweight and high strength and with the ability to be custom fitted to limbs, a cast/splint/brace can be easily custom fitted without undue disturbance to the animal. It can also be shaped into complex shapes (as described in greater detail below) in situ so the animal does not need to be transported. It can also be scaled up or down in size as necessary to be used with smaller animals.

Protective Gear

The system, in a preferred embodiment, provides a custom formable protective gear system that is far superior to previous systems. The protective gear can be for uses such as athletic gear such as shin guards, wrist guards, etc.; military and law enforcement protective gear, for workplace protection and for any other use where custom formed protection is desired.

Figure 22:
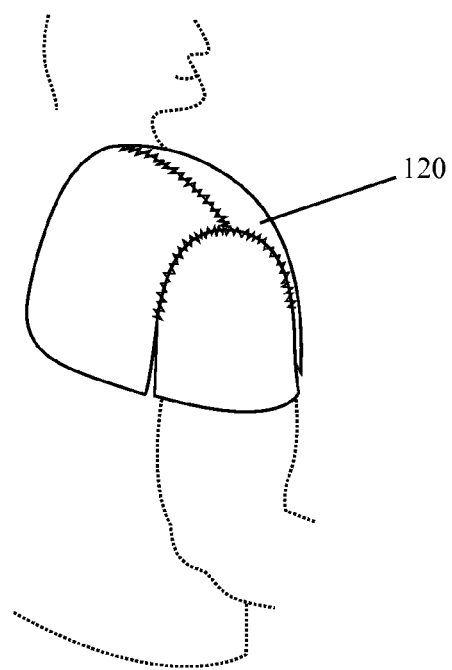
FIG. 22 is an illustration of a protective shoulder pad formed from the composite material.

An example of the use of the composite material of a preferred embodiment of the present invention is a shoulder protector 120, as shown in FIG. 22. The shoulder protector includes multiple parts that are cut, heated and then sewn together (in a process described in greater detail below). The assembled parts are then heated and custom fitted to the body of a user to provide protection to the shoulder area.

Figure 23:
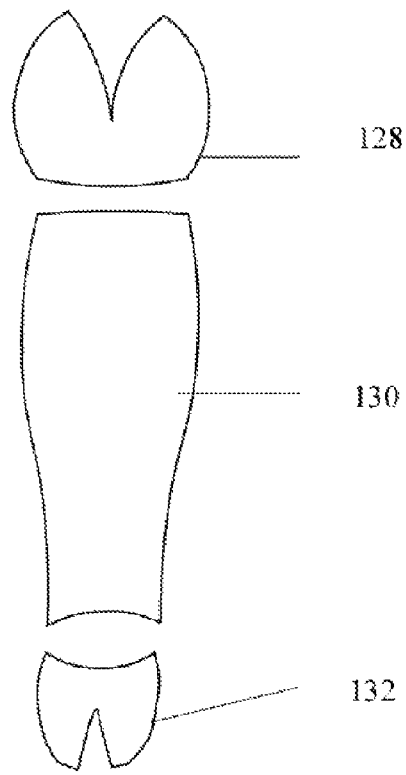
FIG. 23 is an illustration of the components of a protective shin guard formed from the composite material.
Figure 24:
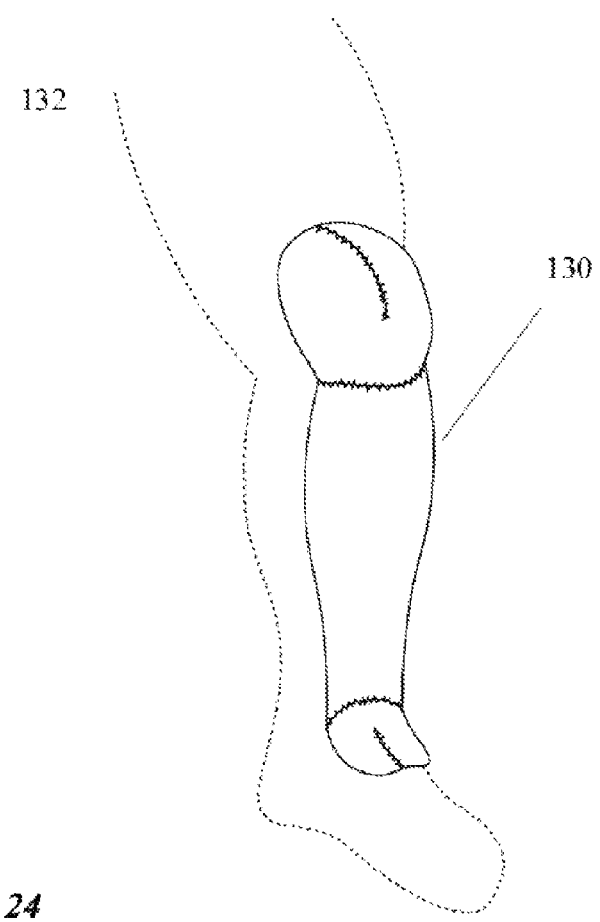
FIG. 24 is an illustration of the assembled protective shin guard.

Another example of a use of the composite material is a shin guard used in many sport activities and law enforcement and military applications to protect a person's shins and knee from damage. As shown in FIGS. 23, 24, multiple parts 128, 130, 132 are formed from the composite material, then heated, and sewn to produce thin profile closely fitted product that can be later heated and fitted precisely to the body. A knee cap and foot protector is incorporated using multiple parts darts and hot sewn seams.

Figure 25:
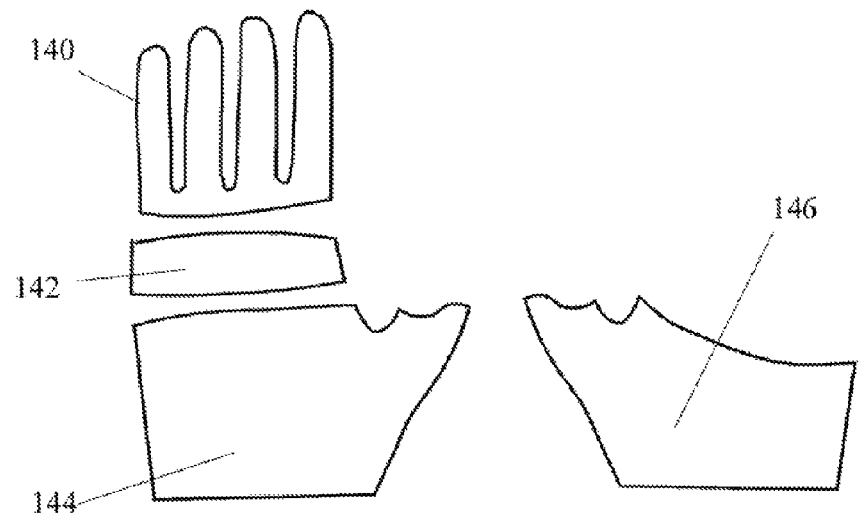
FIG. 25 is an illustration of the components of a protective glove.
Figure 26:
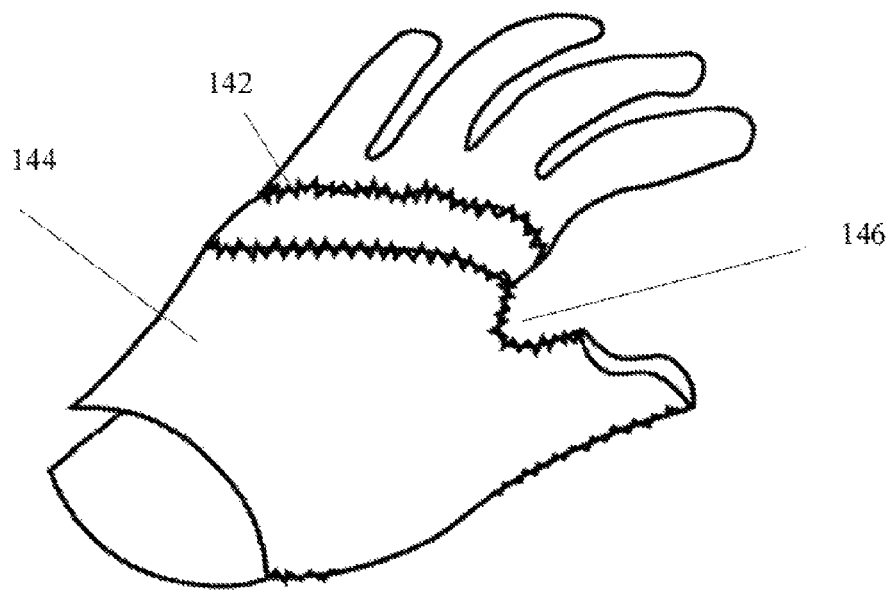
FIG. 26 is an illustration of the assembled protective glove.
Figure 27:
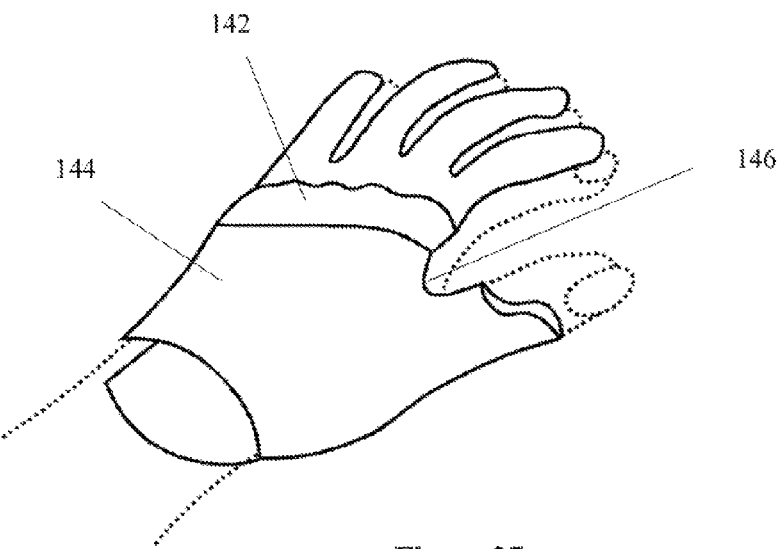
FIG. 27 is an illustration of the protective glove being molded on a hand.

FIGS. 25-27 show a protective glove used in athletics, law enforcement or the military that has a complex multi part interior construction that is made from the preferred embodiment composite material sewn together while hot. As shown in FIGS. 25, 26, multiple parts 140, 142, 144 and 146 are formed from the composite material, then heated, and sewn to produce a thin profile closely fitted protective glove that can be later heated and fitted precisely to the body. This demonstrates how tiny curved edge parts can be sewn together when hot and pliable using standard sewing machine methods. This would not be possible with rigid plastics alone. The finished glove can be heated to 200 degrees Fahrenheit and put on the hand. Then, the wearer can flex the hand and fingers to the desired position most commonly used, such as holding a hockey stick, shield or baton and hold that shape until the item cools providing a custom fitted strong supportive three dimensional fitted product, Once again, this process would be most difficult to achieve using standard materials and methods. Other types of protective gear may be created as well for equestrian uses, industrial and construction gear, geriatric protective products and many other uses.

The protective gear system of this preferred embodiment enables the protective gear to be pre-laminated, pre-shaped or in blank sheets and provided in sizes according to a desired use, such as for protecting a wrist, arm, knee, neck or other body location. The system is then easily customized to the particular user as discussed below. The system, in a preferred embodiment, also allows the protective gear to adjusted as necessary by the user. This adjustability also allows the protective gear to be customized to the particular body part being supported.

The protective gear system is heated, preferably with dry heat (although hot water may be used as well), to become thermoformable for shaping within a few minutes. The protective gear system of this preferred embodiment at temperatures between 160 degrees Fahrenheit to 250 degrees Fahrenheit (the Target Temperature) is pliable for ease in shaping but still is able to maintain some degree of stiffness so not to be overly fluid, as would be reached beyond the glass transition temperature of the material. Other Target Temperature ranges may be used as well with other materials. The system can then be placed on the patient without burning or causing discomfort to the user during this process. The relatively low density foam inner layer insulates the high density hot middle plastic layer from the body. The skin, having a higher density than the foam, actually cools the foam more rapidly than the foam can transfer heat to the skin thus protecting it from burning at the temperatures used. This system which is preferably dry heated is then formed to the exact shape desired for that particular user easily and without the need of specialized skill using a method described below.

Heating Systems

Figure 28:
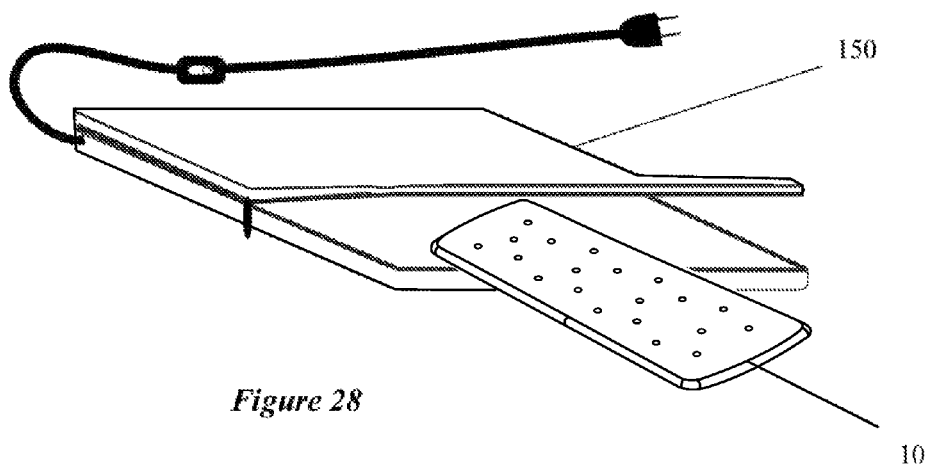
FIG. 28 is an illustration of a heating unit for use with the composite material.
Figure 29:
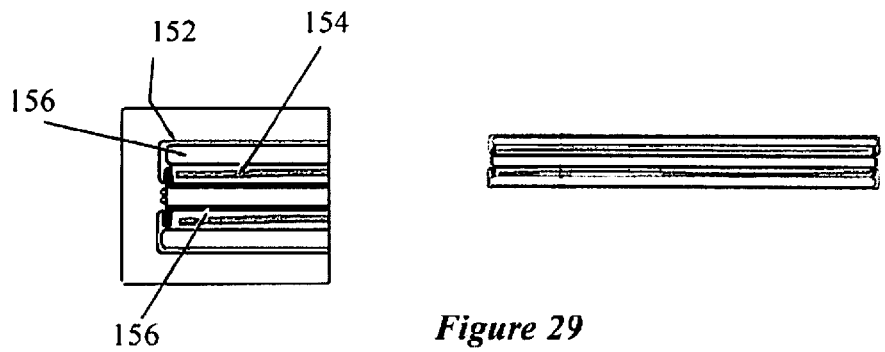
FIG. 29 is a cutaway view of the heating unit.

The present invention also, in a preferred embodiment, provides a heat source for heating the splints to the Target Temperature as described above in order to shape the system to the body part. One preferred embodiment of the heat source, as shown in includes a heating pouch 150 as shown in FIGS. 28, 29, that is easily stored and transported. The heating pouch includes an outer insulation layer 152, opposing heating elements 154 in a sheet fashion and a liner bag 156, preferably durable on the outside and non-stick on the inside, that holds the heating element and insulation. The heater elements can be made of electrical heat wire or heating foil or other electrically activated design. The heater bag 150 is easily opened to accept the splint and closes during the heating process. A closure system such as hook and loop, zipper of buckles closes the bag to hold in heat. The heater element is connected to an electrical power source, either 110-240 VAC standard plug for connection to an electrical outlet, or a 12 V transformer or a 12V DC battery or vehicle electrical power source and maintains the Target Temperature accurately via a thermostat or heat control device. The heating pouch may also include an optional temperature probe that monitors the temperature applied to the bracing system.

In use, the unitized splinting system 10 is placed in the case between the opposing electric heater elements. The case is activated causing the heater elements to heat the splint 10. Once the splint is heated sufficiently to the Target Temperature and adequately pliable, it is removed for application and forming around the body part.

This heat source case is easily transported and able to be used in hospitals, clinics, training rooms or even on site for treating an injury. Special ovens or chemical reactions are not needed.

Another heat source of a preferred embodiment of the present invention uses an internal heating mechanism built into the unitized splint. This may be an electric grid on one or both sides of the middle layer. This grid is connected to a power supply which supplies electric current to heat the middle layer to the target temperature. Once forming of the splint is complete, the electric current is turned off and the splint quickly cools. This eliminates the need for an external heating device since it is built into the splint.

Figure 30:
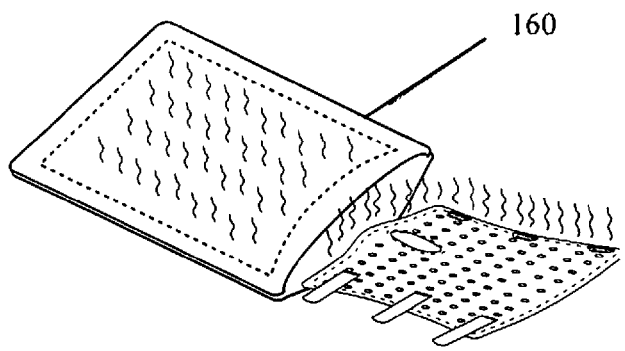
FIG. 30 is an illustration of an exothermic heating unit.

Another heat source under a preferred embodiment of the present invention utilizes an exothermic heat source 160 shown in FIG. 30. A number of chemical reactions exist that produce heat such as carbon/air, Lye/water, air batteries and others. When two or more elements are exposed to each other, the resulting chemical reaction causes heat to be released.

Typical common uses are carbon/air packets used as pocket heaters for cold weather and Lye/water containers used to heat army "meals ready to eat". Similar systems can be used to heat the splints of the preferred embodiment to the Target Temperature by incorporating the heating chemicals into a plastic pouch or bag with adequate room to insert the splint. The chemical reaction is made and the splint heated, removed and applied. The advantage of such a system is that injury often occurs in the field where medics or doctors do not have access to electricity. This method provides a quick simple method to heat the splint in a self contained fashion and apply it in the methods described above.

Other heating means include convection ovens, toaster ovens, radiant lamp heat sources, Infrared heaters and microwave ovens. A convection forced air oven may be used. Wet heat, such as used with previous thermoformable splints may be used as well. This type of heating requires the immersion of the splint into a container of hot water until it reaches the Target Temperature.

Figure 31:
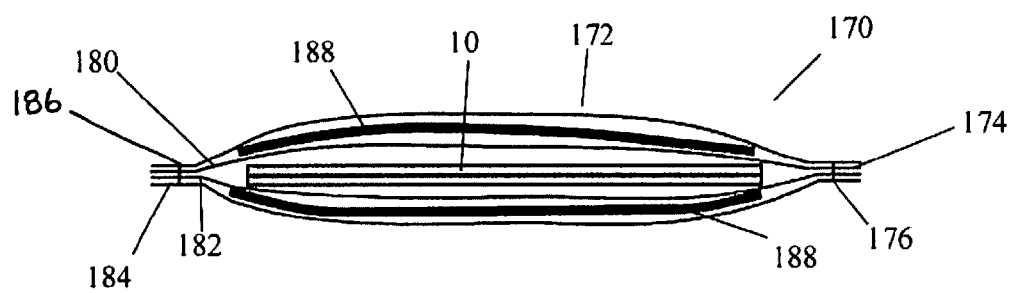
FIG. 31 is a side cutaway view of a microwavable heating unit.
Figure 32:
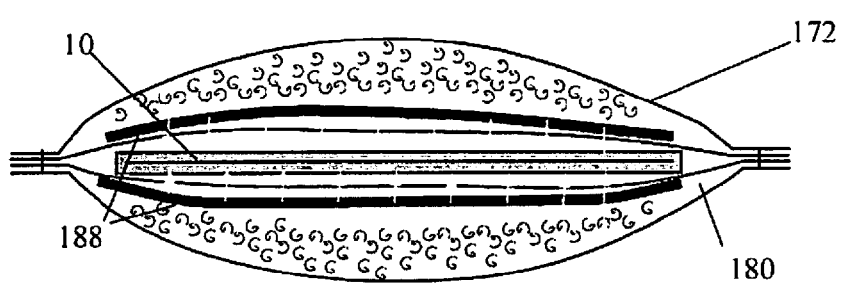
FIG. 32 is a side cutaway view of the heated microwavable heating unit.

Another type of heating systems for use under the present invention utilizes microwave ovens. Typically, microwave ovens do not uniformly heat at a specific temperature. The heating system 170, shown in FIGS. 31, 32 is described for use with a microwave oven, but can also be used with other heat sources as well, such as immersion in hot water and other heat sources as well. In this preferred embodiment, heating system 170 includes a first enclosure 172. The enclosure 172 has an opening 174 along with a sealing mechanism 176, such as sliders used with Zip-Loc bags that forms a waterproof seal on the enclosure. Alternatively, the enclosure can be sealed at the manufacturing with the other components sealed inside. The enclosure 172, in this preferred embodiment is a bag, such as a plastic bag, made of thin polypropylene or other similar materials. The enclosure 172 is of such a size that it can hold the object that is to be heated and formed.

A second enclosure 180 is inserted inside the first enclosure 172. The second enclosure also has an opening 184 with a sealing mechanism 186. The second enclosure may be similar to the first enclosure, such as a plastic bag formed from polypropylene or other materials. Both enclosures should be waterproof and able to withstand temperatures above 220 degrees Fahrenheit.

The heating system 170 also enclosures absorbent materials 188 such as sponges, sheets, paper or nonwoven layers that are inserted within the first enclosure 172 and outside the second enclosure 180. These sheets 188 are moistened with water prior to use. The sheets may be pre-moistened or removed from the enclosure 172, moistened by the user and reinserted in the first enclosure. Alternatively, water can be provided without the absorbent materials.

In one preferred embodiment, the first enclosure 172, the absorbent materials 188 and the second enclosure 180 are bonded together to form a single integral unit. The absorbent materials are bonded between the two enclosures.

The heating system 170 may be provided as a heating system for a user supplied object, or provided as packaging around the object supplied by the manufacturer. In either event, the object 10 that is to be heated and formed is inserted within the second enclosure 180 and sealed therein by sealing mechanism 186. The sheets 188 are moistened either beforehand or at this time and inserted in the first enclosure 172 outside the sealed second enclosure 180.

The first enclosure 172 is sealed by sealing mechanism 176.

The assembled enclosures are then placed in the heat source, such as a common microwave oven. In some instances a larger microwave oven may be necessary if the object to be formed is of a larger size than can be accommodated in a common microwave oven. The microwave oven is then turned on a high operating range. The length of the heating operation depends on the capacity of the oven, the size of the object and enclosures and other factors, but the oven is operated until the water in the absorbent sheets 10 turn to steam. The steam ensures that the temperature within the enclosures are at about 212 degrees Fahrenheit. The relatively short amount of time along with the relatively flexible enclosures will minimize the superheating of the steam so that the temperatures should not rise substantially above 212 degrees Fahrenheit.

Since the enclosures are at about 212 degrees Fahrenheit, the object within the second enclosure will also be about 212 degrees Fahrenheit. The object is held dry by the second enclosure 180 during this process. The heating system 170 is removed from the oven or heat source after the object has been held at the temperature range for a sufficient period of time to ensure that is thoroughly heated at that temperature.

The manufacturer can provide instructions as to the time and temperature range for heating the enclosures if the object is provided in the enclosures from the manufacturer.

Otherwise, the user can experiment to find the optimum time and temperature range.

Once the object has been thoroughly heated, the first enclosure is unsealed to allow the second enclosure to be removed. Then the second enclosure can be unsealed to allow the object to be removed. The object can then be formed into an appropriate shape or custom fit to an object.

It is to be expressly understood that other heat sources may be used as well as microwave ovens. For example, the heating system may be inserted in a container of boiling water to create a similar process. Other heating sources may be used as well, such as exothermic heating sources.

The heating system may also include other embodiment as well. For example, a single enclosure may be used instead of the dual enclosure system. The object is inserted into the single enclosure along with moistened absorbent layers, and heated as described above. The steam from the heated absorbent layers within the enclosure will heat the object to about 212 degrees Fahrenheit. The object may become moistened in this embodiment.

Complex Shaping

The composite material as described above has particular utility for creating complex shaped products. Typically, complex products are formed of separate components that are attached together. Otherwise the product requires complex molding or manufacturing which is not always feasible. The processes for attaching separate components is preferably by sewing when possible. Sewing is often used to form single flat sheets into three dimensional complex shapes. Slits can be formed in the flat sheets which are then gathered and sewn together to form shapes as well as hinges in the products. However, it is often difficult if not impossible to attach plastic components together by sewing as it is difficult to penetrate plastic with sewing needles, particularly if the plastic is rigid and high strength. Also, sewing creates perforations in the plastic, that can lead to tearing of the product.

Figure 33:
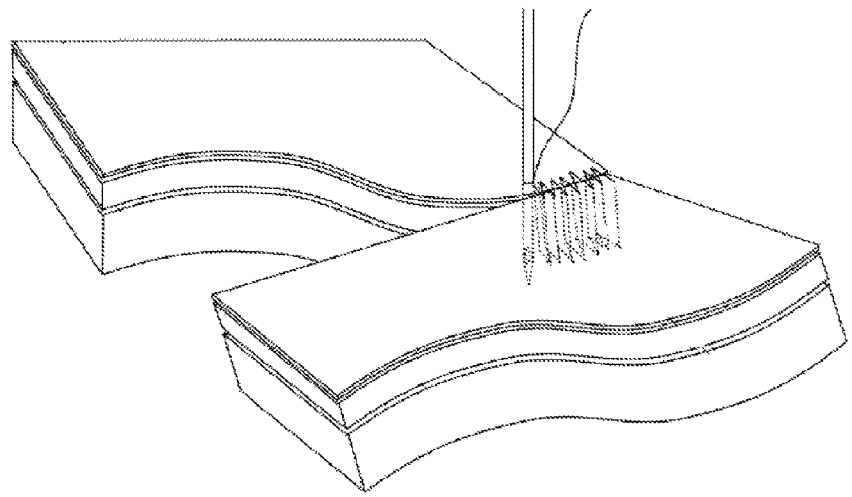
FIG. 33 is an illustration of two components being sewn together.

As shown in FIG. 33, it is difficult if not impossible to sew two rigid materials having contoured edges together. The two contoured edges will not come in close contact with one another. The force required to deform the rigid materials into three dimensional shapes that would cause the contour edges to be joined would not be feasible for most sewing operations.

Thus, previously sewing two rigid materials was rarely done and not possible for very rigid materials with extreme contoured shapes.

This problem has been solved with the preferred embodiment. In use, the composite material 10 can be cut, shaped, sewn and otherwise manipulated into complex three dimensional shapes. The composite material is heated until the middle layer 30 becomes malleable. The outer layers (fabric, cushioned insulative or combinations of the two materials or similar materials) are malleable at ambient, elevated temperatures and maintain the stability of the middle layer 30 as it is malleable, and prevent it from unduly stretching. The outer layers also provide strength to the middle layer to prevent it from tearing as it is shaped, sewn or cut. The stretchable outer layers provide structure for the malleable layer to prevent it from being unintentionally deformed when heated. They also provide a sewing surface that will allow it to pass easily through a sewing machine and allow components formed from the material to be securely joined together. They also insulate the middle layer from being unduly cooled too quickly from contact with the large metal areas of a sewing apparatus. The outer layers have a low coefficient of friction when heated to temperatures up to 220 degrees Fahrenheit. For purposes of this application, the characteristic of having a low coefficient of friction is referred to as being non-sticky or non-tacky.

It is to be expressly understood that while the composite material described above uses a middle heat formable material with foam insulative layers and outer stretchable fabric layers, other embodiments are included under the claimed invention using differing combinations of materials. For example, the composite material may omit the foam insulative layers and use a stretchable material directly attached to the middle layer. Also, the stretchable fabric may be omitted from the composite material embodiment.

It is important to note that the composite layers as described above provide a considerable advantage over attempting to sew a warmed polymer plastic layer that is not covered by fabric and foam layers. The outer layers have a low friction coefficient, unlike melted polymer plastic, so that the composite material will glide through sewing machine surfaces which would otherwise stick to the melted tacky surface of the polymer. Stitching polymer plastic layers together can perforate the material causing weakness and tearing under tension. The stretch fabric material 40 of the preferred embodiment as shown in FIG. 2 includes tiny strong fibers that not only provide strength when affixed to the composite material as the composite material is heated and shaped, it also provides a smooth low friction sewing surface. The sewing needle can penetrate between the tiny strong fibers leaving them undamaged, thus providing a secure seam even while the middle layer is heated and perforated in a weakened and malleable state. Those tiny strong fibers will also prevent the holes in the middle layer from tearing after it is cooled and rigid because they will be bonded and unitized as one. The malleable middle layer will actually bond to the threads once the material cools to its rigid state.

Once the composite material has been heated to a temperature where it is malleable, it can be easily shaped and sewn. The composite material can be cut at ambient temperature and at elevated temperatures more easily. Those pattern shapes can then be sewn together into complex three-dimensional shapes. Once the composite material has been sewn, the joined components can be reheated to further shape by stretching as they are applied to the body. The seams can be pressed flat as well.

Figure 34:
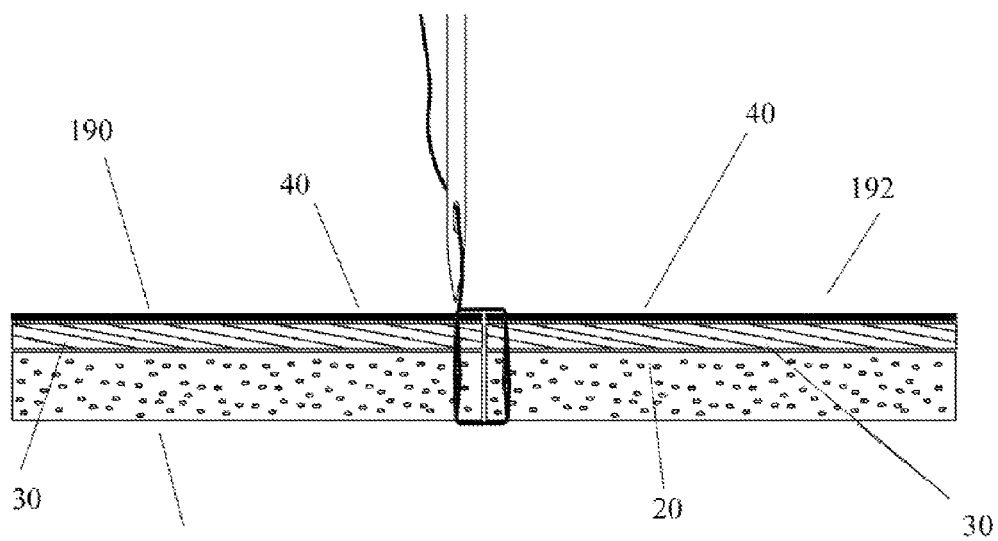
FIG. 34 is a side cutaway view of the sewing of two components formed from the composite material.
Figure 35:
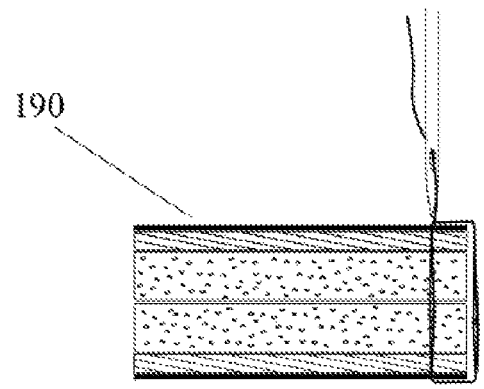
FIG. 35 is a side cutaway view of a particular seam connecting two components.
Figure 36:
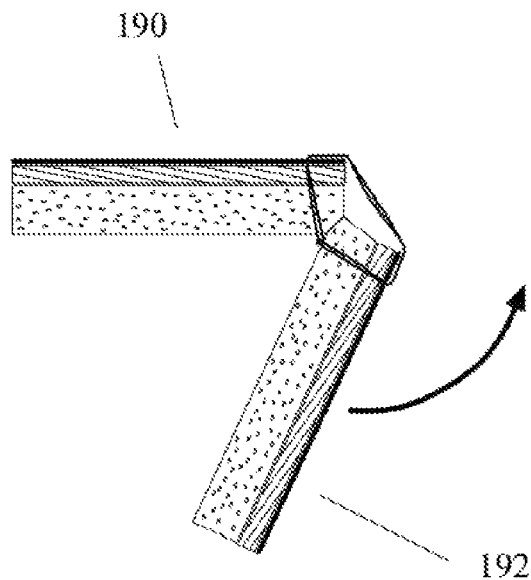
FIG. 36 is an illustration of the seam allowing movement of the two components.
Figure 37:
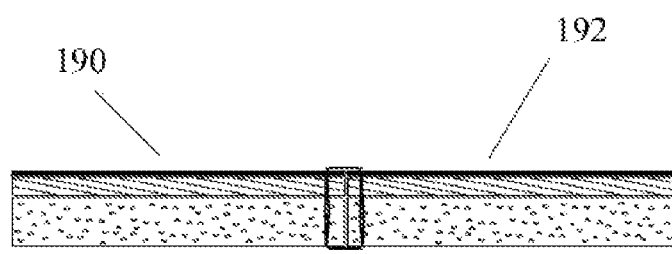
FIG. 37 is an illustration of the seam allowing the components to lay flat.

An example of the sewing process for the composite material is illustrated in FIG. 34. The two components 190, 192 of the composite material 10 are shown in cutaway view in FIG. 34 adjacent to one another. The two components are heated to a temperature at which the middle polymer layers are relatively soft and malleable. The fabric layer 40 and the insulative layer 20 allows the heated material to glide through the sewing surface without sticking The sewing machine stitches a seam through the two components, preferably with a zig zag stitch as shown in FIGS. 34 and 35. This seam may also be made by overlapping the components 190 and 192 and sewing with single or multiple straight common stitches or other more complex stitches as commonly found on sewn products. FIG. 35 shows another useful seam technique. Two layers of the composite material 190 and 192, can be placed face to face and sewn using a zig zag stitch that passes through the layers on one side of the zig and then into air on the other zag side. Once the seam is finished, the joined components can be heated once again to open the seam as shown in FIG. 36, partially opened, and fully opened as shown in FIG. 37. This process is particularly useful when joining complex shapes together with multiple seams such as shown in, but not limited to, FIG. 42, a wrist thumb brace. The sewing step 210 joins the two layers with a seam in the manner shown in FIGS. 35-37. They are sewn face to face and then opened when heated to form a flat seam as in FIG. 37. This seam would be extremely difficult to complete, otherwise, considering the small area of the thumb hole and the limited area provided for a sewing machine to operate.

Essentially, once the composite material is heated to a temperature where the middle layer is malleable, it can be handled similar to a stretch fabric to form desired shapes and fitted body coverings. Then, once it is cooled to room temperature, the resulting shape is an extremely rigid structure due to the rigidity of the middle layer and the three dimensional form whose bent surfaces provide structural strength. This provides a unique composite material that has wide-ranging applications.

The final shaped product can be repeatedly reheated to allow it to be manipulated, joined, sewn and formed into complex shapes and to conform to complex surfaces such as the body. Hot plastic materials alone tend to stretch out and not return to their original shape. When heated, they would burn the skin as they are sewn and applied to the body or handled. They can become extremely tacky and difficult to manipulate. The unique composite material 10, when heated, can be stretched, compressed and bent into very complex shapes. The stretch fabric layers 40 cause the heated composite material to stabilize about a complex shape as well as to pull tight about the shape to create a close form fit. The middle layer can also be formed from a polymer mix that varies so that differing stiffness can be achieved. Also the thicknesses of the middle layer can be varied to provide differing stiffness.

The composite material of the present invention has particular use in medical applications, particularly for orthopedic use. For example, a spica brace is often used to treat thumb and wrist injuries. A thumb wrist spica brace is a type of orthopedic support device used to immobilize the thumb and wrist while allowing other digits freedom to move. It is used to provide support for thumb injuries (ligament instability, sprain, muscle strain, and broken or cracked small bones), gamekeeper's thumb, skiers thumb, osteoarthritis, de Quervain's syndrome, thumb sprains, post-operative use, and post-removal of casting of the hand/thumb.

Figure 42:
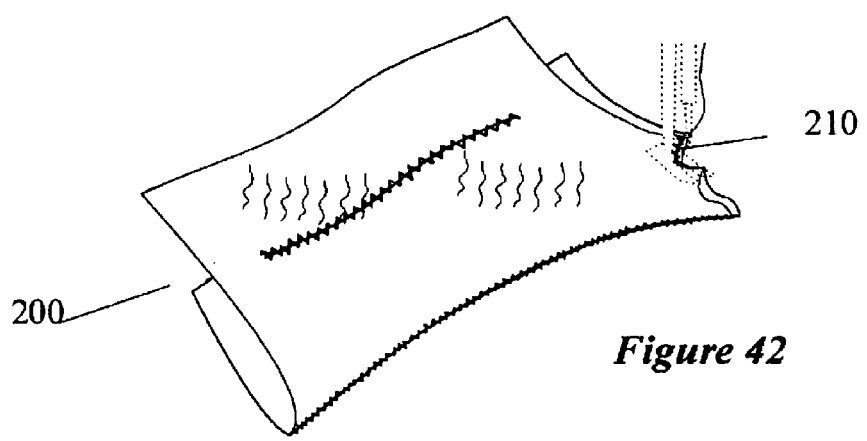
FIG. 42 is an illustration of the components being sewn to form a spica brace.

A spica brace is difficult to properly fit to the patient and is typically custom made in suta by assembling various materials. Some pre-made products for this use are also used but less common. As shown in FIG. 42, a spica brace is a complex shape, since it must support and maintain the thumb, wrist and arm in proper relation to one another, be adjustable in circumference and fit very closely to prevent movement. In suta made braces of this nature require complex assembly of parts on the body and are typically made of fiberglass casting material or poly caprolactone sheet that are hand cut, formed and assembled on the body. Elastic banding and hook and loop closures are the norm which are adhered or riveted in place. Braces of this nature would never be sewn and require great knowledge, practice and time (about 30 minutes) to construct. Pre-made braces of this type are typically sewn of a number of different soft fabrics, elastic fabrics, non stretch fabrics or strapping and sometimes include soft foam/fabric laminates. Then, stiffening ribs or pre-formed or malleable rigid supports are inserted into the sewn item. The sewing is always done on soft materials, not rigid supportive material because it is too difficult to sew rigid material into three dimensional shapes required to fit the body. Occasionally, a soft fabric will be sewn to rigid material, however this varies greatly from sewing complex pieces of rigid materials to each other into three dimensional shapes. In both cases above, the result is a complicated combination of soft and rigid, stretch and non stretch, and strapping materials joined by cumbersome means and multiple parts that provide a product that is less than desirable to wear.

The composite material of a preferred embodiment enables a spica brace to be made of a single composite material sewn together with clean smooth seams that form the base shape. Simple or complex closure mechanisms such as hook and loop, lacing systems or other means can be sewn directly to the warm pliable and durable composite material. The finished product can then be heated and instantly formed and custom fitted directly on the patient due to its stretch and pliability. The result provides a much more wearable item that is thin, supportive, perfectly fitted, waterproof and non absorbent, radiolucent, lightweight and covered with a soft and colorful fabric, When compared with in suta product, far less labor, knowledge and time is required by the practitioner. Compared to pre-made braces, the result is more custom fitted, less bulky and complicated and more comfortable to wear. The five or so minutes required to heat and apply the composite material product of a preferred embodiment varies little from the application of other pre-made products.

Figure 38:
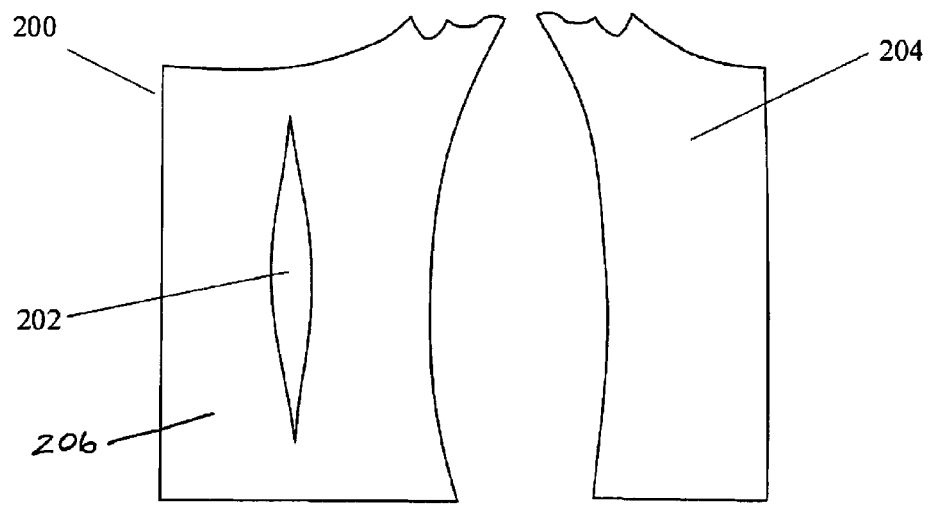
FIG. 38 is an illustration of two components being blank cut.
Figure 39:
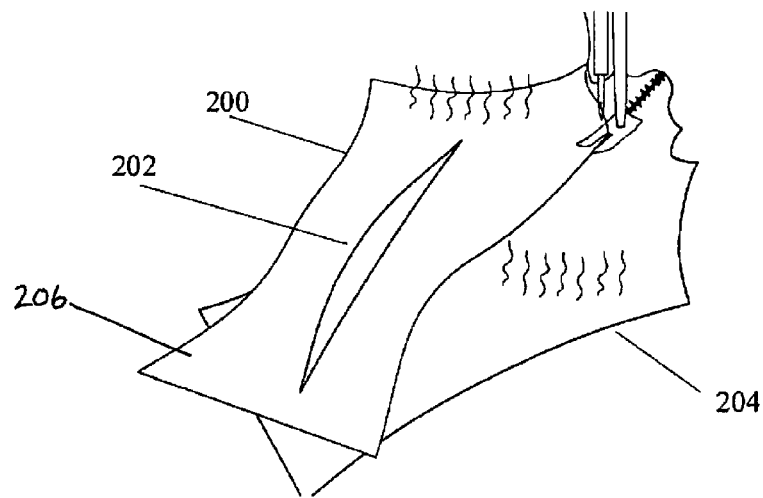
FIG. 39 is an illustration of the two components being sewn together.
Figure 40:
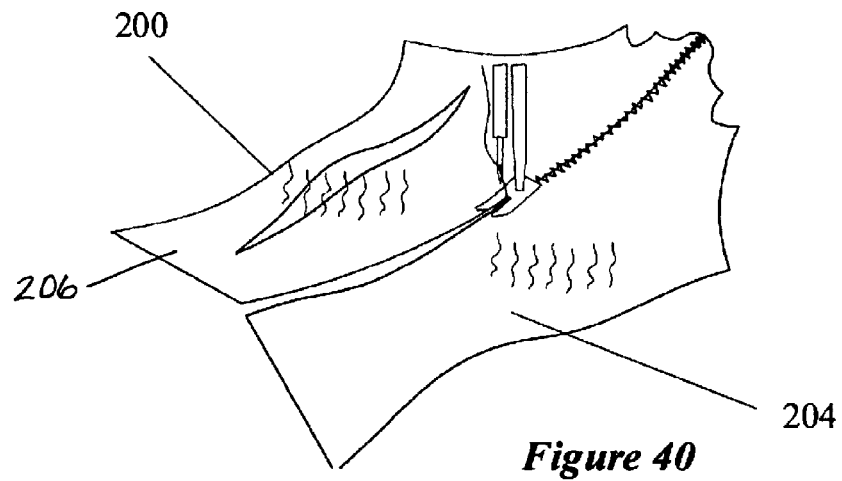
FIG. 40 is an illustration of the two components being sewn while heated.
Figure 41:
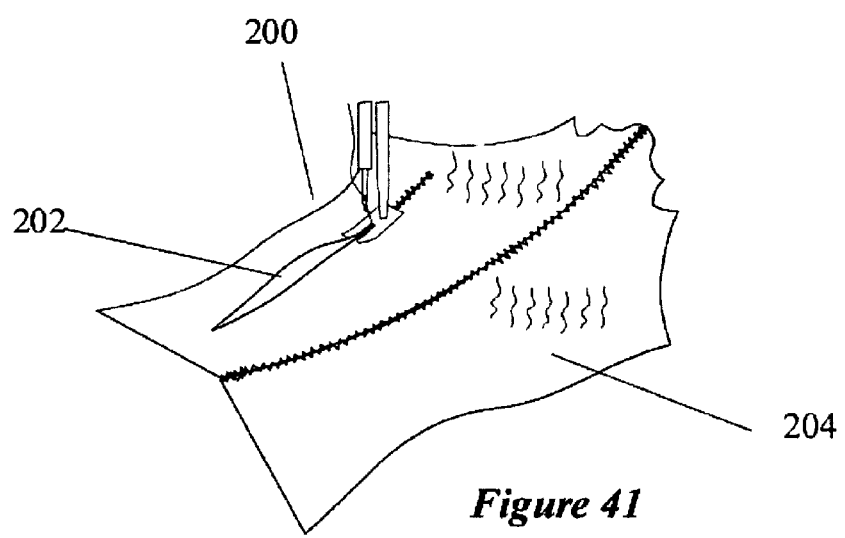
FIG. 41 is an illustration of the components being sewn to form a complex shape.

As shown in FIG. 38, the construction of a thumb wrist brace 200 is cut from two blank sheet of the composite material 10 with contours and aperture 202. The flat sheet composite material parts can be die cut, cut with scissors, computer operated blade, laser, water jet or other production means. The parts are heated to a temperature at which the middle layer is malleable. For example, the composite material may be heated at a temperature of 180 to 200 degrees Fahrenheit for 30 seconds to three minutes using a heat press, oven, heat lamps or other heating means. The material is malleable at this temperature for a sufficient time to allow the parts to be sewn together by means of standard sewing machines. Zig Zag seams may be used to join pieces butted edge to edge. Zig Zag stitching may also be used to sew parts face to face along the edge which is then folded open when still warm to form a flat seam. This method is particularly useful when sewing small sharply curved edges together such as shown in the FIG. 42 of the thumb wrist spica which would otherwise not be possible to sew with rigid sheet. If necessary, the material can be reheated to allow further sewing, attachment and forming processes to occur. It is key to note that the processes described in this paragraph would not be possible to perform with a heated polymer plastic sheet alone as it would not pass through the sewing machine presser foot and feed apparatus because the surface would be sticky causing friction and gumming of the sewing machine and the stitching would perforate and weaken the polymer. The laminated outer layers of fabric and foam stabilize the inner layer, reduce friction and provide durability for sewing.

The completed brace, shown in FIG. 42, can be custom fitted to the patient by heating the completed brace, forming about the patient and allowing it to cool into a custom fitted rigid shape supporting the patients joint. The brace can be reheated as necessary to achieve a comfortable fit on the patient.

FIG. 22 shows another product made using the preferred embodiment. This protective shoulder pad uses three parts cut from flat composite material that are heated to pliability and sewn together with a zig zag stitch with the parts butted edge to edge. The result is a product that is generally shaped as the shoulder but when reheated to 200 degrees Fahrenheit and applied to the shoulder it stretches to fit the body perfectly without pressure points or loose areas. Sewing this item of rigid sheet as is the know art would be difficult is not impossible. In addition, forming it to the body without the insulating foam layer would be problematic due to discomfort. Having the outer stretch fabric layer and heat formable inner layer laminated to the mid polymer layer allows easy forming without a lot of pressure applied. A simple elastic wrap applied when warm would shape the part accurately to the body.

Another example of the use of the composite material of a preferred embodiment of the present invention is a shin guard used in many sport activities and law enforcement and military applications to protect a person's shins and knee from damage. As shown in FIG. 23, multiple parts the composite material are cut, heated, and sewn to produce thin profile closely fitted product that can be later heated and fitted precisely to the body. A knee cap and foot protector is incorporated using multiple parts darts and hot sewn seams.

Attachable Closure System

Figure 43:
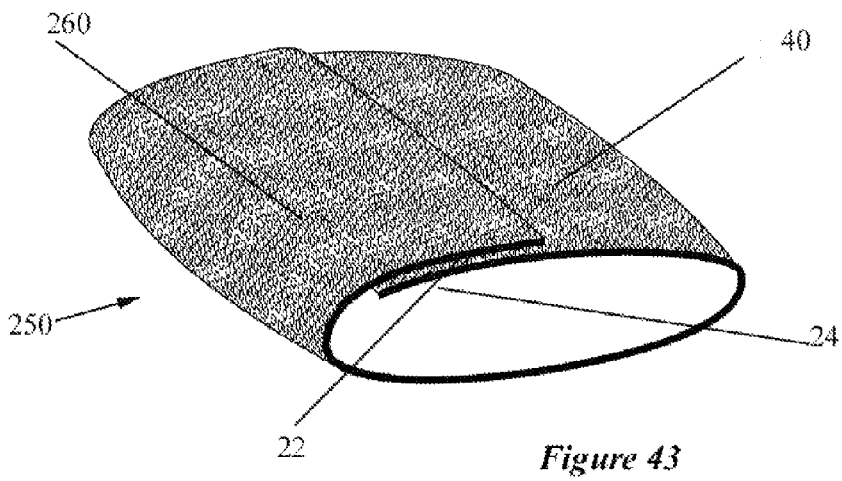
FIG. 43 is an illustration of a brace having an outer layer of unbroken loop fabric.

The closure system 250 of this preferred embodiment is able to be attached at desired points on many different products. The product used in this descriptive embodiment is a brace 10 (although any other orthopedic product such as a cast could be used as well as non-orthopedic products) that has side edges 22, 24, such as the cast disclosed in copending application Ser. No. 12/013,449 which is incorporated herein by reference. The outer layer of the brace of this preferred embodiment, includes a layer 260 of unbroken loop fabric, such as Velcro®, distributed by Velcro USA, Inc as shown in FIG. 43. The outer layer may be entirely formed of unbroken loop fabric 260 shown in a preferred embodiment in FIG. 43.

The unbroken loop fabric layer 260 can be adhesively bonded, molded, sewn or otherwise attached onto the cast. Alternatively, the fabric layers may also be bonded as an integral part of the outer layer 40. Other methods of securing to or forming with the unbroken loop fabric layers onto the product can be used as well.

Figure 44:
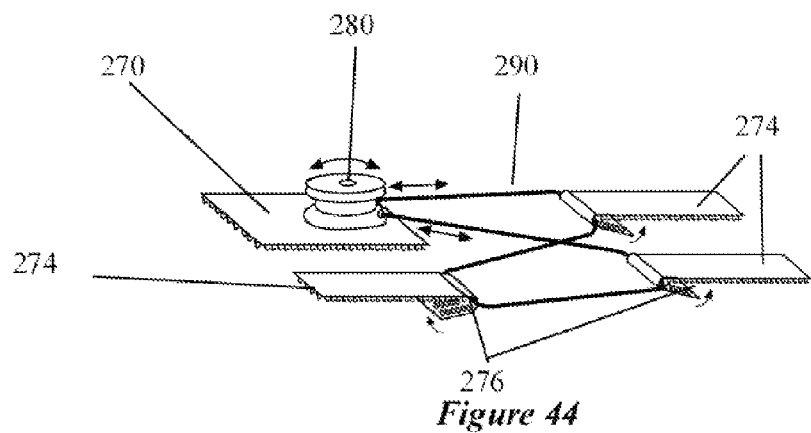
FIG. 44 is an illustration of an attachable closure mechanism.

The attachable fastening mechanism, as illustrated in FIG. 44, includes a strip 270 with corresponding hook elements that will engage and secure to the unbroken loop fabric is fastened to the bottom surface of a fastening mechanism 280. In this embodiment, the fastening mechanism 280 include cable reel elements such as the cable reel attachment systems distributed by BOA Technology Inc. and described in the U.S. Patents and Published Applications incorporated by reference above. The cable reel 280 can rotate to tighten the lace and may be pulled vertically to release the lace. Other fastening mechanisms may be used as well including cord locks, cam cord locks, traditional lacing bows, ratchet lace systems, and other lacing methods. An alternative system using ski boot buckles such as ratchet strip buckles can also be used in a similar fashion with pieces of hook fabric at either end as described in greater detail below.

A series of elongated strips 274 with hook fastening strips are also used in this preferred embodiment as illustrated in FIG. 44. These strips 274 are mounted at selected locations at spaced intervals along the edges of the cast or other product and extend over the edges. These sections engage with the unbroken loop fabric 260 on the products and are secured thereon. The end of the strips 274 which have a loop surface 276 are then doubled over to engage the hook surface onto the base hook surface of strip 274 to form loops to secure the elongated flexible member 290 as described in greater detail below.

Figure 45:
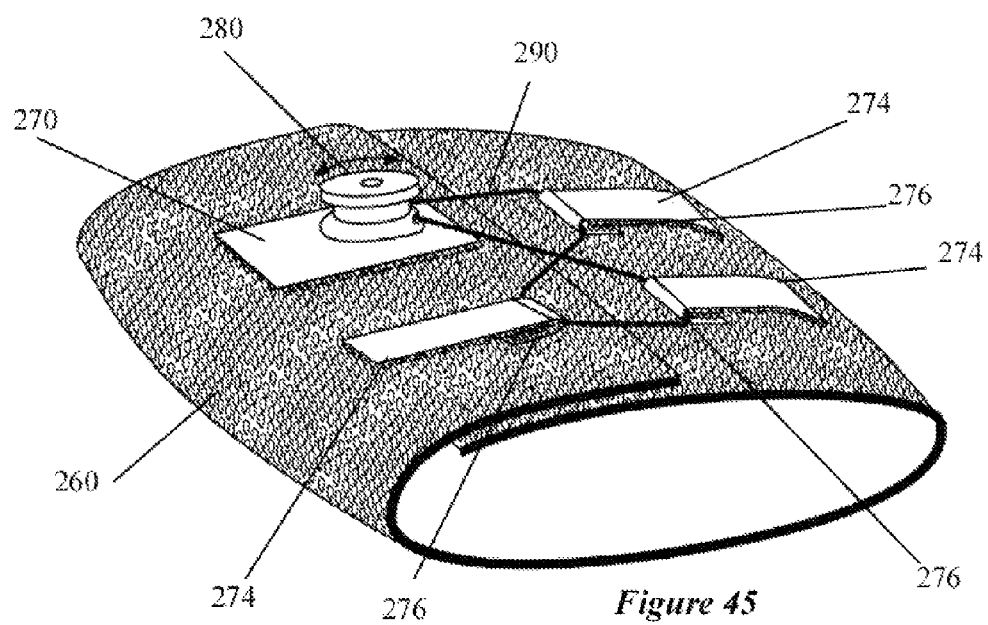
FIG. 45 is an illustration of the attachable closure mechanism assembled onto the brace.

The fastening mechanism, such as the cable reel 280, can then be attached at a suitable location, by engagement of the hook engaging strip 270 with the unbroken loop layer 260 on the cast as shown in FIG. 45. The guide strips 274 are also attached to the unbroken loop layer 40 at desired locations by engagement with the hook members on the strips. A flexible elongated member, such as a cable or lace 290 can then be threaded through the loops 276 and around the cable reel. The lace 290 can then be pulled taut by rotation of the cable reel to draw the edges of the cast together. It is to be expressly understood that the term lace also includes cable, line or any other elongated flexible member suitable for use with the present invention. The shear stresses on the hooks and loops of the loops 276 and on the fabric layer 260 along with the hook engaging members of strips 270 and 274 provide the force to securely engage the hooks and loops against one another since hook loop fastener tends to be quite strong in shear.

It is also to be expressly understood that the unbroken loop fabric layers described herein could be corresponding hook elements instead with the described hook elements replaced with the unbroken loop fabric layers.

Figure 46:
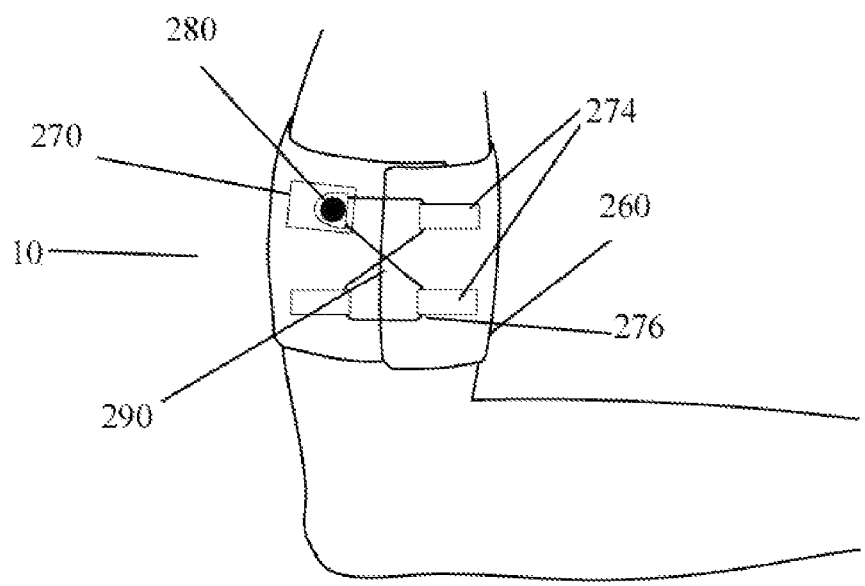
FIG. 46 is an illustration of the assembled brace on a patient.

The assembled product can then be placed over a body part, such as the example shown in FIG. 46. The support 10 is slipped over the body part, and the cable reel 280 is rotated to tighten the lace 290 through the loops 276 to tighten the overlapping edges around the body part until the support is secure in place over the body part. Alternately, the brace or cast can be applied to the body part without the closure system in place which can later be installed as desired in situ.

Figure 47:
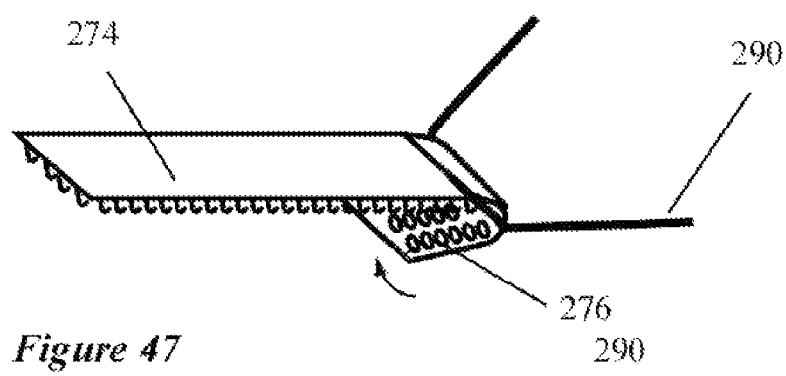
FIG. 47 is a close up view of a component of the attachable closure mechanism.
Figure 48:
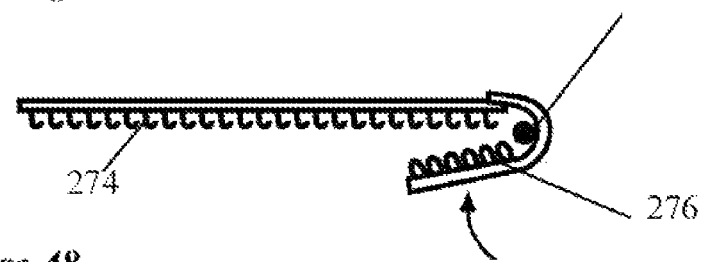
FIG. 48 is a side view of the component.
Figure 49:
FIG. 49 is another side view of the component.

The fastening strips 274 as shown in FIGS. 47-49 are able to easily form a guide for the cable or lace 290. The fastening strips 274 include an end portion having unbroken loops for engagement with the hooks on the fastening strips. The end portion is doubled over to engage the hooks to form a loop or guide 276 for guiding the lace 290.

Figure 50:
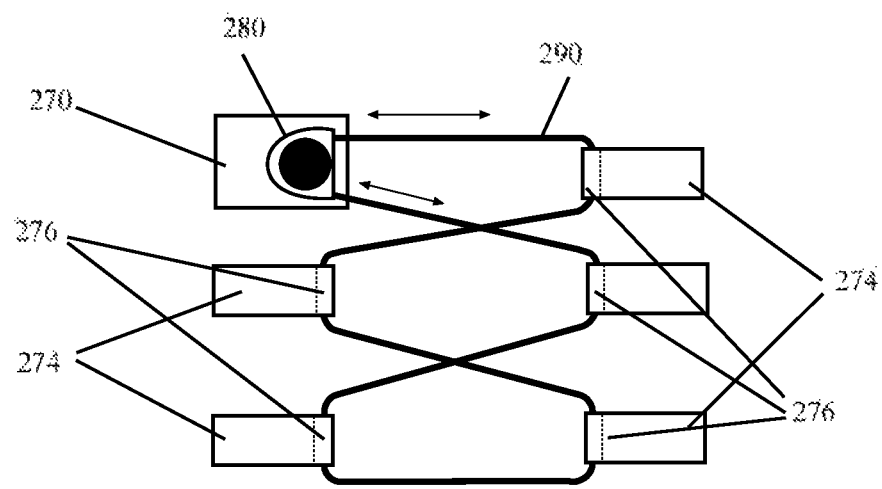
FIG. 50 is an illustration of one configuration of the attachable closure mechanism.
Figure 51:
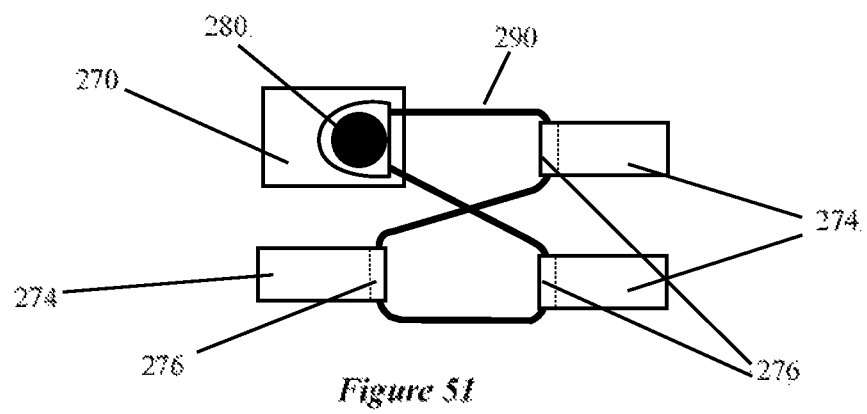
FIG. 51 is an illustration of another configuration of the closure mechanism.
Figure 52:
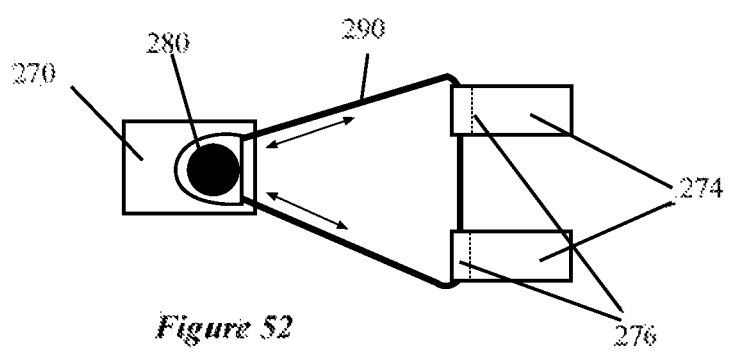
FIG. 52 is an illustration of another configuration of the closure mechanism.

The attachable lacing system can be configured any number of ways to address particular needs. For example, as shown in FIG. 50, the attachable lacing system includes the fastening mechanism 280 on the hook strip 270 along with five guide fastening hook strips 274 attached in parallel, opposing locations. Another configuration as shown in FIG. 51 uses three guide fastening strips 274 with the fastening mechanism 280. The configuration as shown in FIG. 52 uses two spaced guide fastening strips 274 opposite the fastening mechanism 280.

Figure 53:
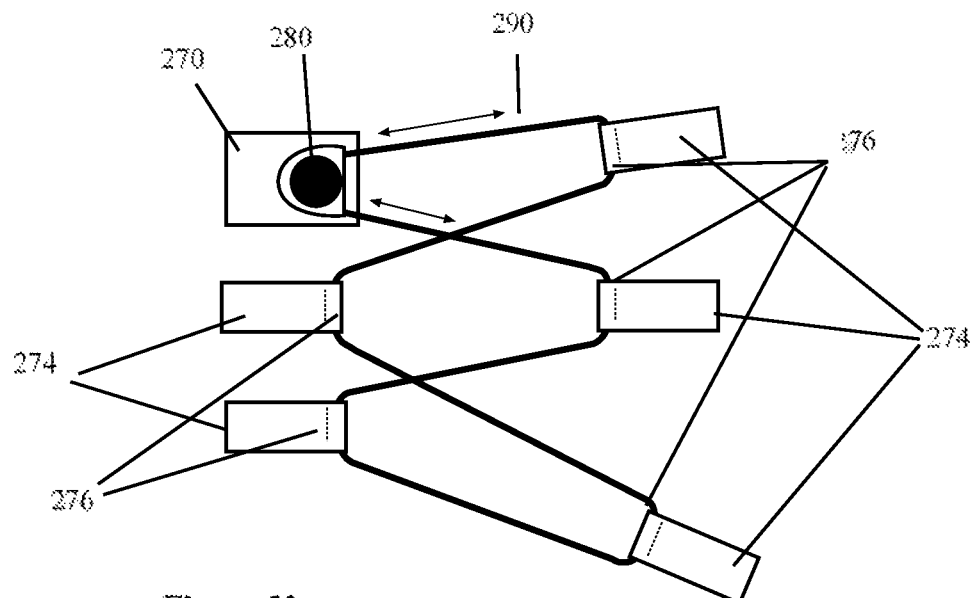
FIG. 53 is an illustration of another configuration of the closure mechanism.
Figure 54:
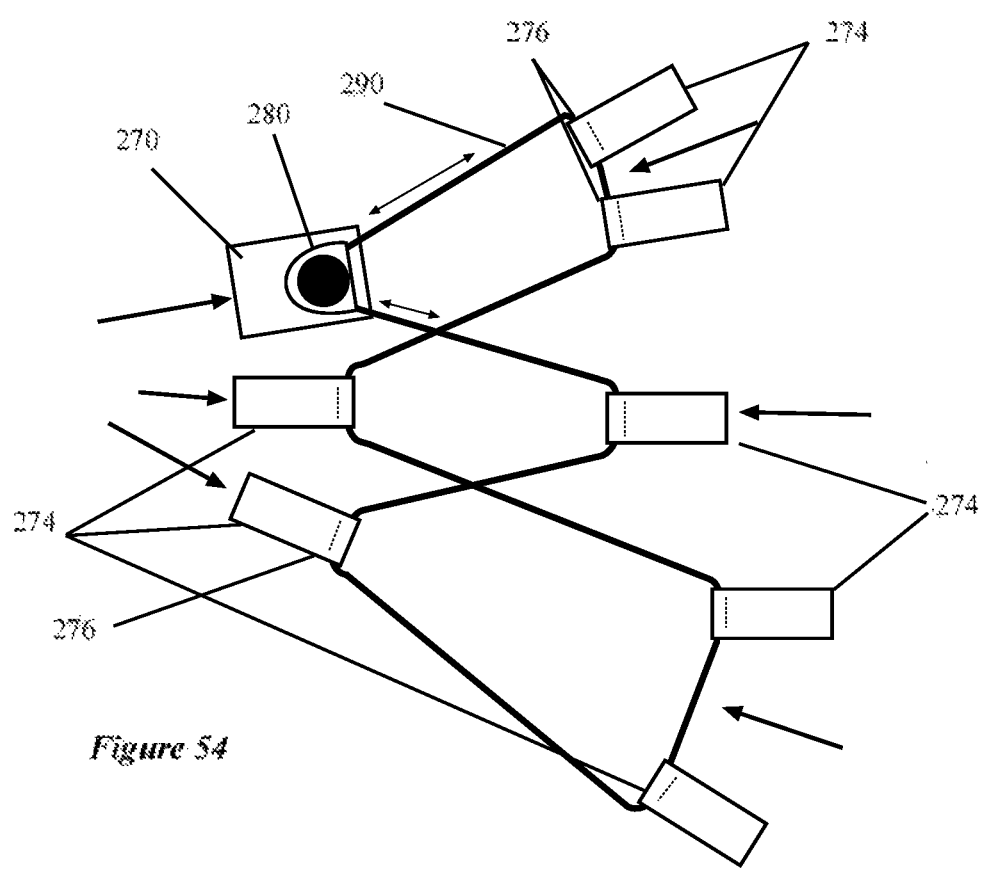
FIG. 54 is an illustration of another configuration of the closure mechanism.

The attachable lacing system can also be configured in angular orientations as may be necessary for complex shaped products. Examples of this are shown in FIGS. 53 and 54. The tension from the lace 290 against the guides 276 on the guide strips 274 will pull the hooks attached to the unbroken loop surface regardless of the angle to secure the strips to the product and pull it closed as desired. This flexibility of orientation of the guides 276 allows the closures to pull at different angles thereby achieving several closure operations all at once.

Alternative Embodiments

Figure 55:
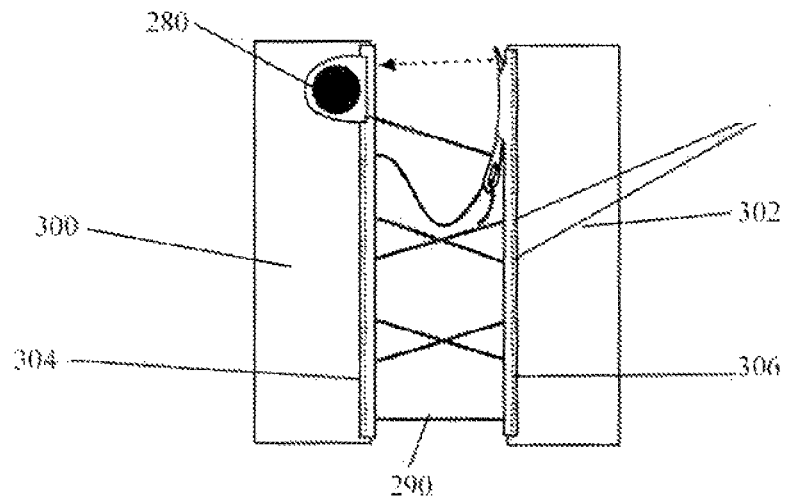
FIG. 55 is an illustration of another closure mechanism.
Figure 56:
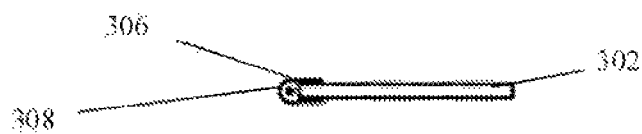
FIG. 56 is a side cutaway view of a component of the closure mechanism.
Figure 57:
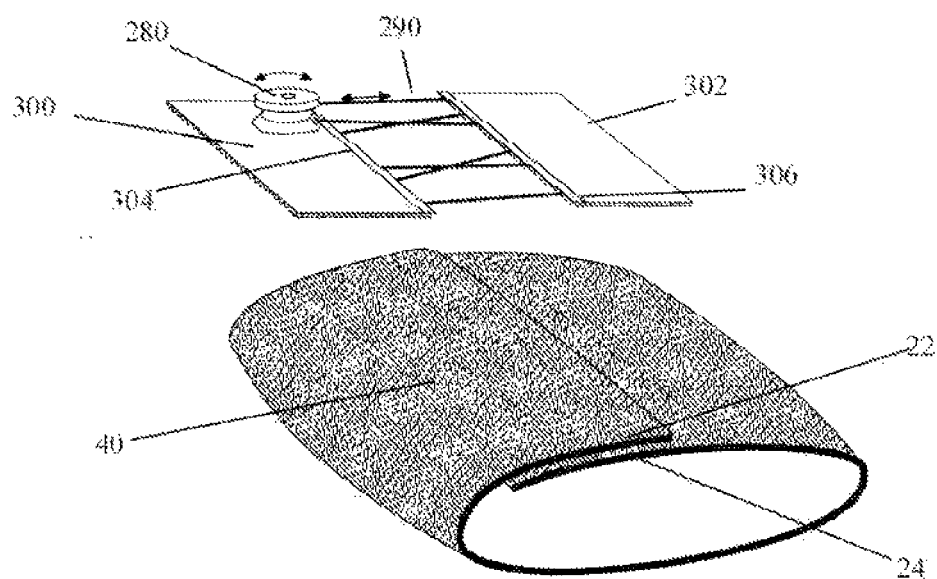
FIG. 57 is an exploded assembly view of the closure mechanism on the brace.
Figure 58:
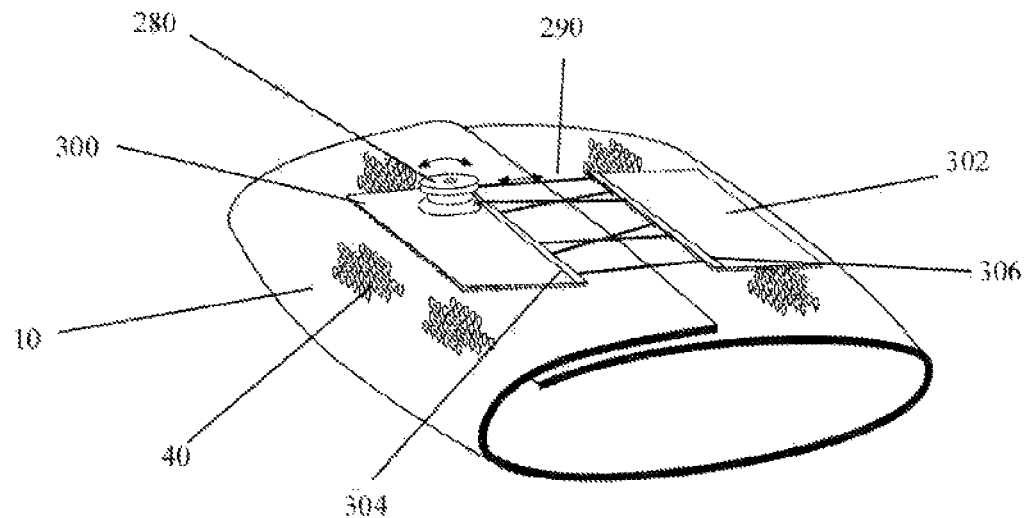
FIG. 58 is an illustration of the assembled brace.
Figure 59:
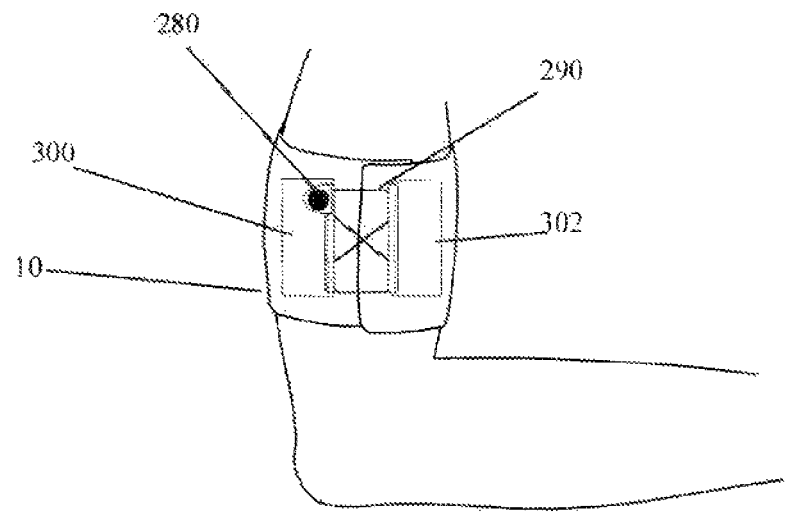
FIG. 59 is an illustration of the brace on a patient.

An alternative embodiment is illustrated in FIGS. 55-59. The attachable system of this embodiment uses two strips 300, 302 of material with hook members on their back side. The fastening mechanism 280 is affixed to one of the strips 300 by adhesives, sewing, or by any other manner. Two ribbons 304, 306, such as nylon webbing, fabric or any other material, are attached to the inner edges of the strips 300, 302. The ribbons 304, 306 form an aperture along the edge of the strips 300, 302 to allow the lace 290 to be inserted there through using a sewing needle or awl to insert the lace into the ribbon aperture 308 in whatever lacing pattern desired as shown in FIG. 58. Holes 308, are shown in FIG. 55, are formed by the needle and cable at spaced apertures along the length of the ribbons 304, 306 to allow the lace to exit and enter to form a lacing pattern. A cross section view, FIG. 56 shows the lace 290 as it passes inside the ribbon 306, affixed to the strip 302.

The pre-assembled attachment mechanism can then be simply attached on the product at the desired location by engagement of the hooks on the bottom side of each of the strips 300, 302 with the unbroken loop fabric 260 on the product 10 as shown in FIGS. 57, 58. The fully assembled product and attachment mechanism can then be slipped into place and secured by tightening the lace 290 by the fastening mechanism 280. The tension on the lace 290 not only secures the product to the body, as shown in FIG. 58, but also secures the hooks on the strips 300, 302 with the loops 260 on the product. One side of the attachment mechanism 302 can then be lifted from the unbroken loop surface and allows ease of entry and exit to the device.

Figure 60:
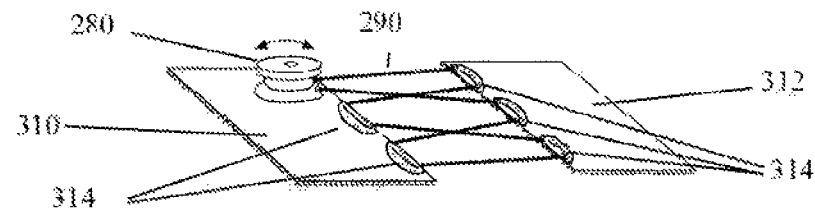
FIG. 60 is an illustration of another closure mechanism.

Another embodiment of the attachment system is illustrated in FIG. 60. This embodiment is similar to the embodiment described above with the use of two parallel strips 310, 312 having hook elements on their bottom side. However, this embodiment uses plastic (or metal) guides 314 attached along the edges of the strips 310, 312. The guides 314 are attached by adhesives, sewing or any other manner to the strips. The fastening mechanism 280 is also secured to one of the strips as described above. The lace is then wound around the guides 314 and the strips 310, 312 are secured to the product by engagement with the hook elements on the strips with the loops on the product.

Figure 61:
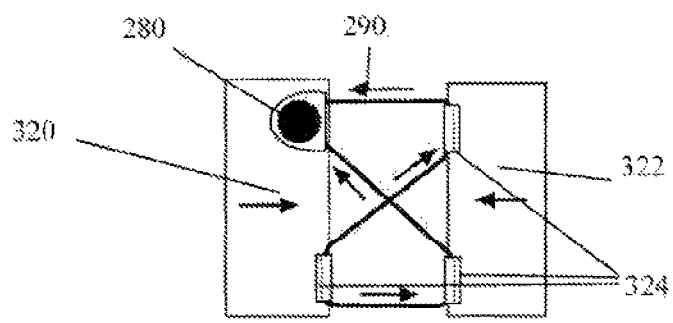
FIG. 61 is an illustration of another closure mechanism.
Figure 62:
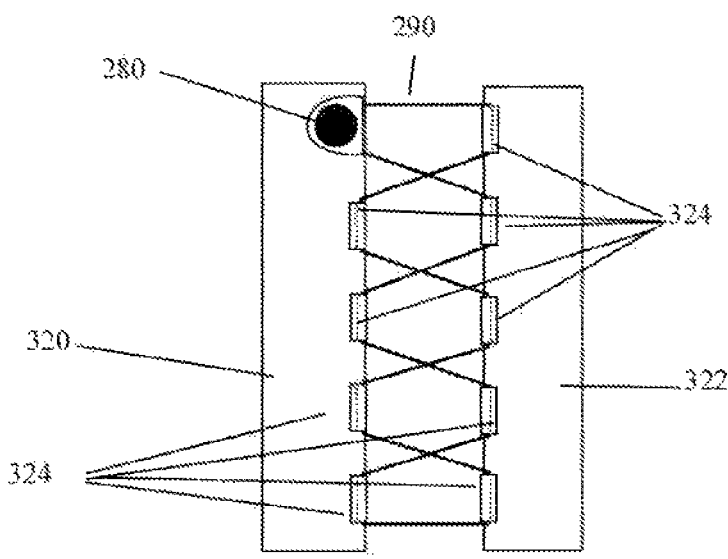
FIG. 62 is an illustration of another configuration of the closure mechanism.

Another embodiment of the attachment system is illustrated in FIGS. 61, 62. This system is similar to the systems described above using two parallel strips 320, 322 having hook elements on their back side with a fastening mechanism 60 secured to one of the strips. This embodiment however uses guides 324 formed from webbing spaced along the edges of strips 320, 322. The webbing guides are secured to the strips by sewing, adhesives or any other manner of fastening. The lace 290 is inserted through the guides in a lacing pattern as shown. The strips 320, 322 are secured to opposing edges of the product by engagement of the hook elements on the strips with the loops 260 on the product. The tension from the lace as the product is secured to the body also secures the hooks with the loops.

Figure 63:
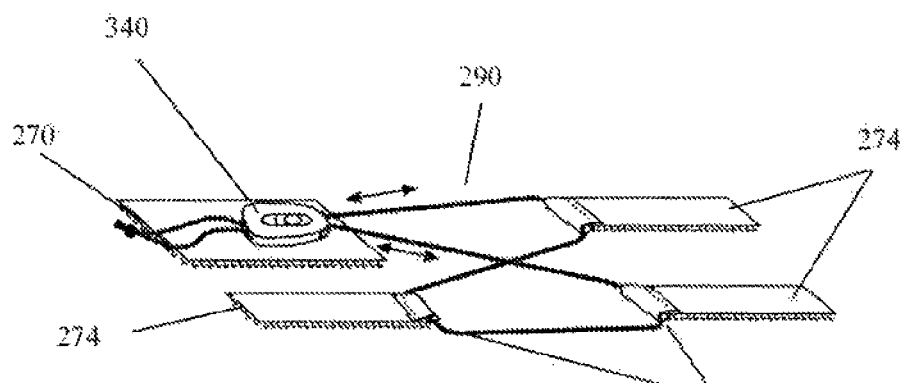
FIG. 63 is an illustration of another closure mechanism.
Figure 64:
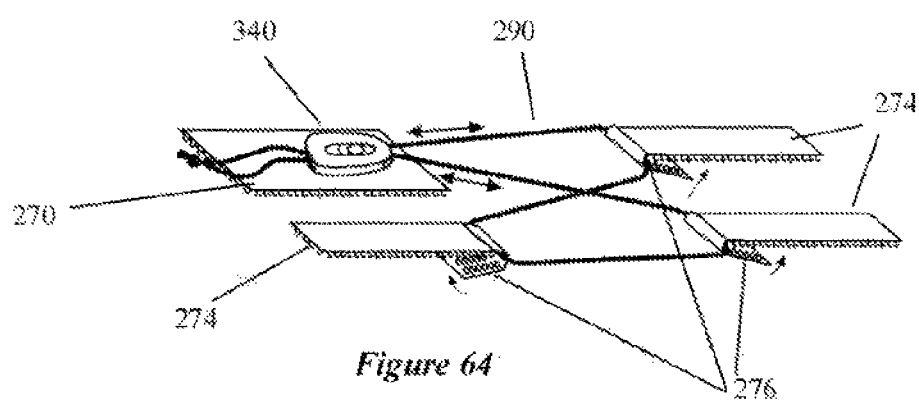
FIG. 64 is another view of the closure mechanism.
Figure 65:
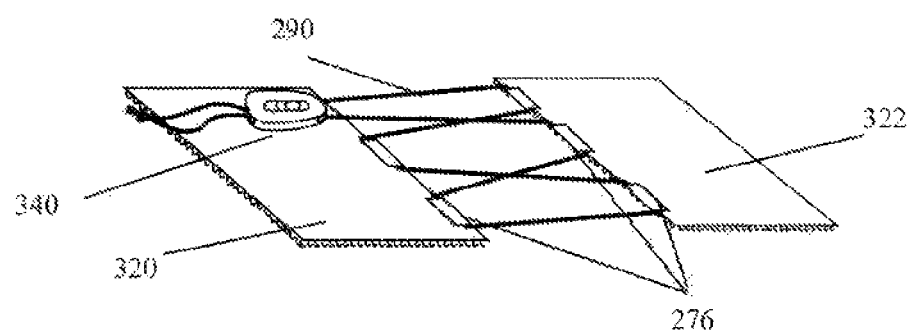
FIG. 65 is an illustration of another closure mechanism.

In another embodiment, a cable lock 340 may be used in lieu of the cable reel described in the earlier embodiments. The lace 290 is manually pulled taut and secured by a cam mechanism in the cable lock 340. The cable lock is mounted to the fastening strip 270 as shown in FIGS. 63, 64 or to one of the strips as shown in FIGS. 64, 65 by sewing, adhesives, molding or any other fastening method. The guide fastening strips 274 can be used, as discussed above, with the lace 290 inserted through guides 276 and the cable lock 340. The strips 270, 274 can then be configured and secured to the product by the engagement of the hook elements on the strips 270, 274 with the loops 260 on the product. The product is then placed onto the body and the lace 290 is pulled through the cable lock 340 until sufficient tension secures the product in place and fully engages the hooks on the strips with the loops on the product. The cam on the cable lock 340 will secure the tensioned lace until such time as it is released.

Figure 66:
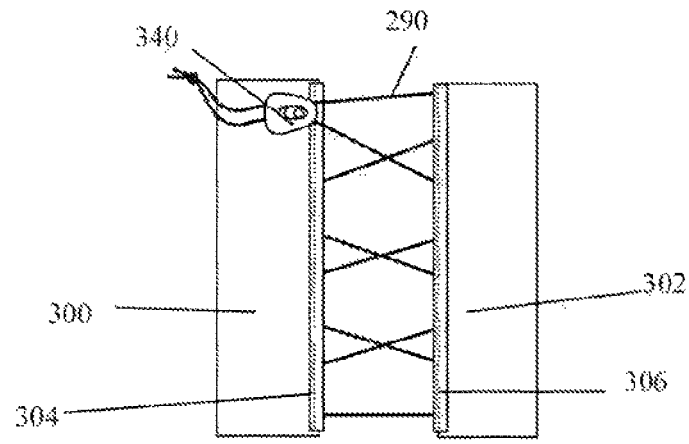
FIG. 66 is an illustration of another closure mechanism.
Figure 67:
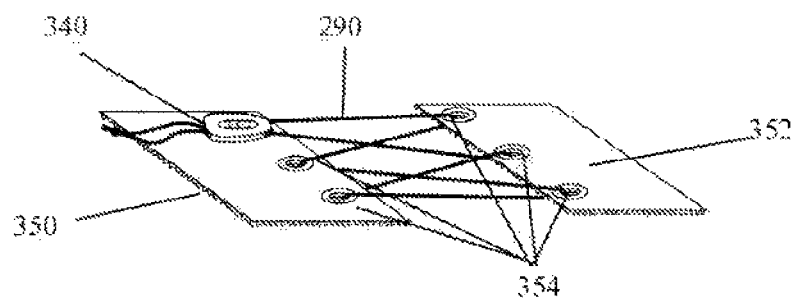
FIG. 67 is an illustration of another closure mechanism.
Figure 68:
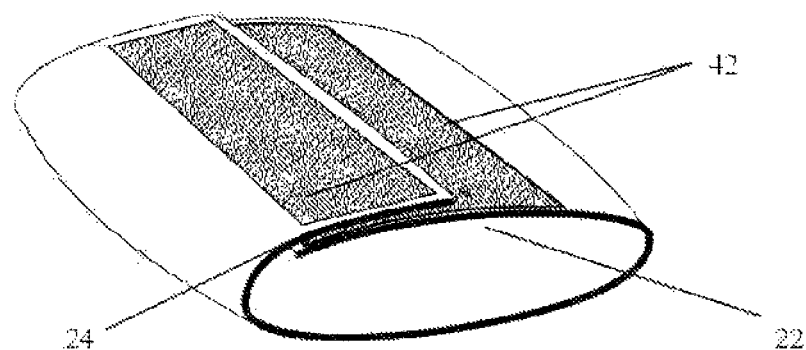
FIG. 68 is an illustration of a brace with portions of unbroken loop fabric.

Alternative embodiments of the cable lock mechanism 340 are illustrated in FIGS. 66-67. The embodiments show the use of the cable lock mechanism 340 with opposing strips 320, 322 and plastic guides 324 as shown in FIG. 62, with the parallel strips 300, 302 and ribbons 304, 306 allowing the lace to be inserted through the ribbons to form guides as discussed above, and with parallel strips 350, 352 with grommets 354 with the lace inserted through the grommets Another alternative embodiment is illustrated in FIG. 68. Sections of unbroken loop fabric 42 is strategically placed where needed as shown in FIG. 26 where sections 42 are affixed to the edges 22, 24 of the brace. The strips 270, 274 can then be easily located and attached at locations on these sections 42 of unbroken loops.

Figure 69:
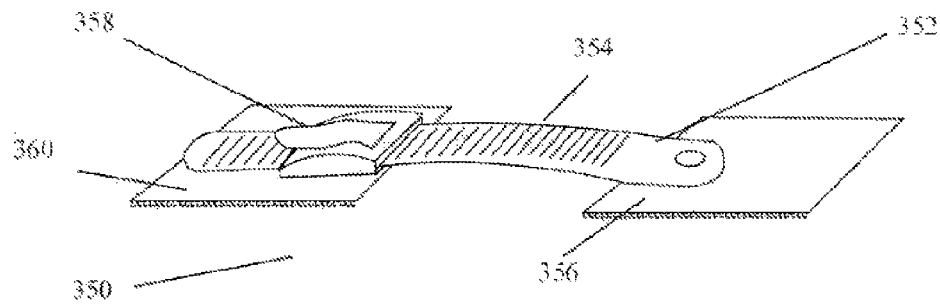
FIG. 69 is an illustration of another closure mechanism.
Figure 70:
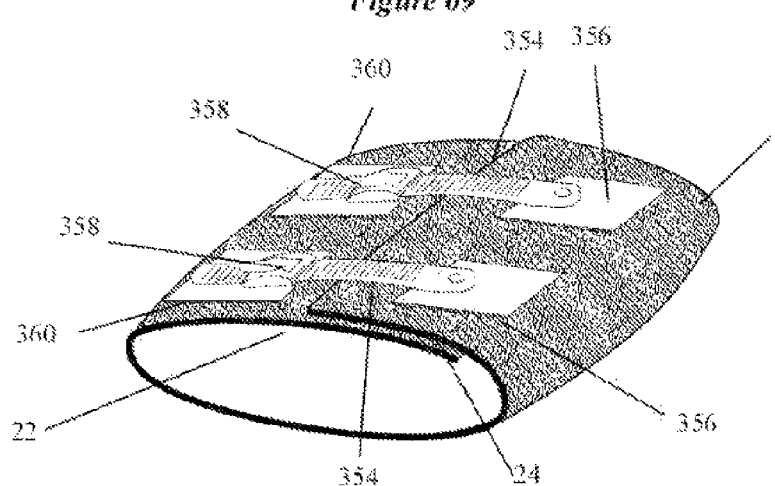
FIG. 70 is an illustration of the closure mechanism assembled onto a brace.

Another embodiment of the attachable closure system is illustrated in FIGS. 69, 70. This embodiment uses a ratchet buckle mechanism 350. A strap 352 having a series of spaced teeth 354 is mounted on strip 356 having a plurality of hook elements on its underside. A ratchet buckle 358 is mounted on strip 360 which also has a plurality of hook elements on its underside. The strip 360 with the ratchet buckle 358 is attached on one edge 24 on the brace while the strip 356 with the strap 352 is attached on the opposing edge 22 by engagement of the hook elements with the unbroken loop fabric 260. The brace is mounted to the body of the patient and tightened by the ratcheting of the strap 352 by the buckle 358. The tightening of the brace and the strap will cause the hooks to further engage securely in the loops of the brace. Other variations and embodiments may be used with the invention as set forth in the claims to provide fastening mechanisms beyond the reels and cable locks, and with guides beyond those discussed herein. Other configurations of the attachment systems are also included in the claimed inventions. The embodiments discussed herein are provided merely for descriptive purposes to explain the claimed inventions and are not meant to limit the scope of the claimed inventions.

Figure 71:
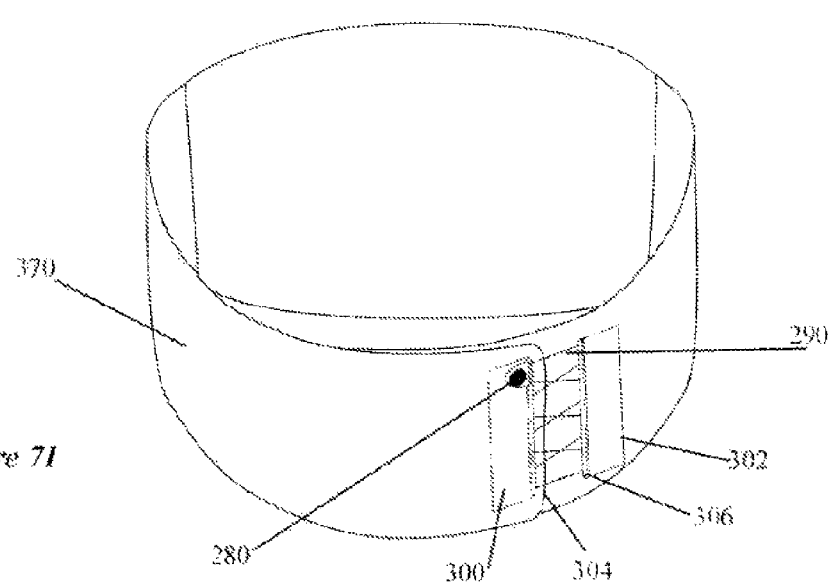
FIG. 71 is an illustration of the attachable closure mechanism on a back brace.

Other examples of the use of the attachment mechanism are shown in FIGS. 71-72. One example is the use of the attachment mechanism on a back brace 370 as shown in FIGS. 71, 72. The back brace 370 includes at least portions of unbroken loop fabric 260 affixed near the opposing edges of the back brace. The attachable securing system having opposing strips 300, 302 with hook elements on their bottom sides, guides 304, 306 formed of ribbon fastened to the edges of the strips 300, 302 and a fastening mechanism 60 is initially mounted near the opposing edges of the brace 370. The brace can then be resized to fit on a smaller person, as shown in FIG. 72, by releasing the tension on the lace 290, removing the strips 300, 302 from the brace, cutting off a portion of the brace 370 and repositioning the strip 302 at a location further along the length of the brace, so that the brace is effectively smaller. This repositionable closure system allows custom configuration of products such as this because it may be easily remove allowing the brace to be custom fitted, cut to size or specially configured and then the closure system is reapplied in a different position as desired. The closure system also allows easy entry and exit by lifting and reattaching either side portion 300 or 302 from the unbroken loop portion 370.

Another embodiment of a use of the claimed invention is illustrated in FIGS. 73, 74. In this example, the attachable securing system is mounted on a leg/foot brace 380. The securing system has the fastening mechanism 280 mounted on an upper portion of the brace 380 by the hook elements on the strip 270 engaging with unbroken loops 260 on the brace and guide fastening strips 274 spaced along the upper portion of the brace 380. The lace 290 is tensioned to secure the upper portion of the brace about the leg while leaving the foot portion relatively un-tensioned for comfort or a second attachable securing system can be added on the lower portion. FIG. 74 illustrates this securing system reconfigured so that the foot portion of the brace is tensioned as well.

This unique system allows products to be created in situ with minimal manufacturing capability. The product can be formed to the desired shape and then the attachment mechanism can be secured at the desired locations to provide a fully functional product. This system has particular utility with the orthopedic products disclosed in copending patent application Ser. Nos. 12/013,449 and 12/181,272. These products use a unique product that includes a heat formable inner layer surrounding by insulative foam materials and fabric such as unbroken loop fabric. This composite material enables a product to be formed and custom shaped about a body part by heating the product, placing the heated product about the body part and applying pressure to custom form the product. The attachment mechanism of the present invention provides further utility by allowing the securing system to be attached in situ to provide additional customization for the product.

In one embodiment of the present invention, the orthopedic product is provided in a blank sheet or partially formed product that has an unbroken loop fabric surface. The blank is then cut and roughly formed to fit about the body part to be supported. Then the fastening system is attached to the product by securing the guides as discussed above or other fasteners to the unbroken loops on the product. The closure device can also then be attached, such as the cable reel, cable lock, buckle or other device by engaging the hooks on that device with the loops on the product. A lace, strap or other tensioning device can then be guided through the fastening system and securing device as discussed above. The device can then be tightened about the body part by the fastening and securing devices as discussed above.

The above unique combination of cast features provides an attachment system for orthopedic products that can be easily custom formed to the patient on site without the need for specialized training or skills. The resulting product is patient compliant and can be adjusted as needed to increase compliance with its use. The adjustability can also decrease soft tissue injuries.

The attachable fastening system of this preferred embodiment may be provided for use with orthopedic products that are relatively flat shape or generally in the shape for a specific body part, such as a wrist, ankle, knee or other body part as well as in general sizes, such as large, medium, small. The adjustable overlap also contributes to this custom fitting as discussed above.

The claimed inventions provide a unique product and processes for creating and using custom fitted products that can be readily created and assembled in situ. The composite material provides a unique product that can be customized to provide a secure and comfortable fitted product. The composite material can be easily formed into complex shapes. It is to be expressly understood that the above described embodiments are intended for explanatory purposes and are not intended to limit the scope of the claimed inventions.

What is claimed is:

1. An orthopedic product for supporting a body part, comprising:
 a composite material including:
  an inner layer defining an area configured to face toward the body part;
  an outer layer defining an area configured to face away from the body part, said area of said outer layer being similar to said area of said inner layer; and
  a middle layer substantially coextensive with said areas of said inner layer and said outer layer, and sandwiched between said inner layer and said outer layer, said middle layer comprising a polymer layer that is thermo formable within a target temperature range and substantially rigid at temperatures below a minimum formable temperature of 130 degrees Fahrenheit;
 at least two contoured edges of said composite material adapted to be positioned substantially adjacent one another; and
 means for directly joining said at least two contoured edges of said composite material while said middle layer is above said minimum formable temperature to form a three dimensional structure that conforms with a corresponding portion of the body part,
 wherein said three dimensional structure includes at least two separate components each formed of said composite material, each component having an edge that forms a distinct one of said at least two contoured edges.

2. The orthopedic product of claim 1, wherein the means for directly joining comprises one or more stitches that sew together at least said middle layers proximate said at least two contoured edges.

3. The orthopedic product of claim 1, wherein said three dimensional structure includes an aperture created within and through said composite material that defines said at least two contoured edges.

4. The orthopedic product of claim 1, further comprising:
 at least two closable edges of said three dimensional structure adapted to be positioned substantially adjacent one another when the orthopedic product is placed upon the body part, said closable edges being distinct from said contoured edges; and
 means for selectively closing said at least two closable edges without directly joining said closable edges.

5. The orthopedic product of claim 1, wherein said inner layer and said outer layer each comprise a foam layer having a lower density than said polymer layer of said middle layer, said foam layer having a coefficient of friction that is not tacky and less than a coefficient of friction of said polymer layer within said target temperature range.

6. The orthopedic product of claim 1, wherein said polymer layer has a hardness within a range of Shore 65D-80D in accordance with ASTM D2240, a tensile strength in the range of 6000-9000 psi in accordance with ASTM D638, an elongation at break of 5% in accordance with ASTM D638, and a flexural modulus of between 270,000-340,000 psi in accordance with ASTM D5023.

7. The orthopedic product of claim 1, wherein said middle layer is integrally formed with said inner layer and said outer layer.

8. The orthopedic product of claim 1, wherein said target temperature range is between a temperature of about 160 degrees Fahrenheit and 220 degrees Fahrenheit.

9. The orthopedic product of claim 1, wherein the three dimensional structure is selected from the set consisting of: a cast, a brace and a splint.

10. A method of manufacturing an orthopedic product for supporting a body part of a patient, the orthopedic product including a composite material comprising an inner layer, an outer layer and a polymer middle layer substantially coextensive with the inner layer and outer layer, the middle layer thermoformable within a target temperature range and substantially rigid at temperatures below a minimum formable temperature of 130 degrees Fahrenheit, the method comprising:
 heating the composite material such that the middle layer is above the minimum formable temperature;
 directly joining a first edge of the composite material to a second edge of the composite material while the middle layer is above the minimum formable temperature so as to form a three dimensional structure that conforms with a corresponding portion of the body part, wherein said three dimensional structure includes at least two separate components each formed of said composite material, and wherein each component has an edge that forms a distinct one of said first and second edges; and
 joining the separate components to form the three dimensional structure.

11. The method of claim 10, wherein joining comprises sewing the first edge of the composite material to a second edge of the composite material such that the middle layer is sewn together along the first edge and the second edge.

12. The method of claim 10, wherein said three dimensional structure includes an aperture created within and through said composite material that defines said first and second edges.

13. A method, comprising:
 causing a composite material to be manufactured and made available to a user, the composite material including: an inner layer configured to face toward the body part and having a perimeter; an outer layer configured to face away from the body part and having a perimeter, said perimeter of said outer layer being similar to said perimeter of said inner layer; and a middle layer having a perimeter that is substantially coextensive with said perimeters of said inner layer and said outer layer, and sandwiched between said inner layer and said outer layer, said middle layer comprising a polymer layer that is thermoformable within a target temperature range and substantially rigid at temperatures below a minimum formable temperature of 130 degrees Fahrenheit, wherein the composite material includes at least two closable edges;
 causing a closure means to be manufactured and made available to the user;
 providing instructions to the user for creating an orthopedic product, including: heating the composite material such that the middle layer is above said minimum formable temperature;
 creating an aperture within and through said composite material that defines a first contoured edge and a second contoured edge, the contoured edges adapted to be positioned substantially adjacent one another;

directly joining the first contoured edge to the second contoured edge while the middle layer is above said minimum formable temperature so as to form a three dimensional structure that conforms with a corresponding portion of the body part;

forming the composite material about the body part while the middle layer is above said minimum formable temperature; and selectively closing the at least two closable edges with the closure means, without directly joining the closable edges.

14. The method of claim 13, wherein the instructions for directly joining the first contoured edge to the second contoured edge further includes instructions for sewing the first contoured edge to the second contoured edge such that the middle layer is sewn together along the first contoured edge and the second contoured edge.

15. An orthopedic product for supporting a body part, comprising:
a closure system including:
a first attachment member having a plurality of hook elements;
a fastening mechanism affixed to the first attachment member;
a second attachment member having a plurality of hook elements;
a guide element affixed to each of said first and second attachment members; and
an elongated flexible member inserted through each of said guide elements and engaging said fastening mechanism; and
a composite material including:
an inner layer configured to face toward the body part and having a perimeter;
an outer layer configured to face away from the body part and having a perimeter, said perimeter of said outer layer being similar to said perimeter of said inner layer and the outer layer including at least one section configured to interface with a hook material as part of a hook-and-loop fastening system; and
an intermediate layer having a perimeter that is substantially coextensive with said perimeters of said inner layer and said outer layer, and sandwiched between said inner layer and said outer layer, said intermediate layer comprising a polymer layer that is thermoformable within a target temperature range and substantially rigid at temperatures below a minimum formable temperature of 130 degrees Fahrenheit, wherein the first attachment member and second attachment member are releasably coupleable to the at least one section of the outer layer of the composite material via the plurality of hook elements of the first and second attachment members so as to create an adjustable and repositionable orthopedic product.

16. The orthopedic product of claim 15, wherein the outer layer comprises a material configured to interface with a hook material as part of a hook-and-loop fastening system.

17. The orthopedic product of claim 15, wherein said fastening mechanism is selected from the set of one or more of: a cable reel mechanism, a lace-lock mechanism and a ratchet buckle mechanism.

18. The orthopedic product of claim 15, wherein said guide element includes: a section of material having unbroken loops secured to said second attachment member and engaging said hook elements of said second attachment member to form a guide loop.

19. The orthopedic product of claim 15, further comprising a guide member affixed to said first attachment member.

20. The orthopedic product of claim 15, wherein said system includes:
a first ribbon attached to an edge on said first attachment member to form a guide element along said edge of said first attachment member; and
a second ribbon attached to an edge on said second attachment member to form a guide element along said edge of said second attachment member that is formed by using a needle or awl to sew said elongated flexible member inserted through each of said guide elements and engaging said fastening mechanism.

21. The orthopedic product of claim 15, wherein said elongated flexible member is selected from the set of: a cable extending through said guide elements and said secured fastening mechanism, and a lace extending through said guide elements and secured to said fastening mechanism.

22. An orthopedic product for supporting a body part, comprising:
a composite material including:
an inner layer defining an area configured to face toward the body part;
an outer layer defining an area configured to face away from the body part, said area of said outer layer being similar to said area of said inner layer; and
a middle layer substantially coextensive with said areas of said inner layer and said outer layer, and sandwiched between said inner layer and said outer layer, said middle layer comprising a polymer layer that is thermo formable within a target temperature range and substantially rigid at temperatures below a minimum formable temperature of 130 degrees Fahrenheit;
at least two contoured edges of said composite material adapted to be positioned substantially adjacent one another;
means for directly joining said at least two contoured edges of said composite material while said middle layer is above said minimum formable temperature to form a three dimensional structure that conforms with a corresponding portion of the body part;
at least two closable edges of said three dimensional structure adapted to be positioned substantially adjacent one another when the orthopedic product is placed upon the body part, said closable edges being distinct from said contoured edges; and
means for selectively closing said at least two closable edges without directly joining said closable edges.

23. The orthopedic product of claim 1, wherein said middle layer is integrally formed with said inner layer and said outer layer.

24. The orthopedic product of claim 1, wherein the three dimensional structure is selected from the set consisting of: a cast, a brace and a splint.

* * * * *